(12) United States Patent
Zhang et al.

(10) Patent No.: US 11,123,189 B2
(45) Date of Patent: Sep. 21, 2021

(54) HEART VALVE PROSTHESIS DELIVERY SYSTEM

(71) Applicant: Suzhou Jiecheng Medical Technology Co., Ltd., Jiangsu (CN)

(72) Inventors: Ji Zhang, Burnaby (CA); Brandon G. Walsh, Kaysville, UT (US); Cheng Yong Yang, Foster City, CA (US); Jinhua Zhu, San Francisco, CA (US)

(73) Assignee: JC MEDICAL, INC., Burlingame, CA (US)

( * ) Notice: Subject to any disclaimer, the term of this patent is extended or adjusted under 35 U.S.C. 154(b) by 183 days.

(21) Appl. No.: 16/240,207

(22) Filed: Jan. 4, 2019

(65) Prior Publication Data

US 2019/0209311 A1 Jul. 11, 2019

Related U.S. Application Data

(60) Provisional application No. 62/781,537, filed on Dec. 18, 2018, provisional application No. 62/756,556, filed on Nov. 6, 2018, provisional application No. 62/614,489, filed on Jan. 7, 2018.

(51) Int. Cl.
*A61F 2/24* (2006.01)
*A61F 2/966* (2013.01)
*A61M 25/01* (2006.01)

(52) U.S. Cl.
CPC .......... *A61F 2/2436* (2013.01); *A61F 2/2412* (2013.01); *A61F 2/2415* (2013.01); *A61F 2/2418* (2013.01); *A61F 2/2463* (2013.01); *A61F 2/246* (2013.01); *A61F 2/2433* (2013.01); *A61F 2/966* (2013.01); *A61F 2002/9665* (2013.01); *A61M 25/0136* (2013.01)

(58) Field of Classification Search
CPC .... A61F 2/2436; A61F 2/2412; A61F 2/2415; A61F 2/2418; A61F 2/2463; A61F 2/2433; A61F 2/246; A61F 2/966; A61F 2002/9665; A61F 2/2427; A61F 2/243; A61M 25/0136
See application file for complete search history.

(56) References Cited

U.S. PATENT DOCUMENTS

| | | | |
|---|---|---|---|
| 7,025,780 | B2 | 4/2006 | Gabbay |
| 7,387,640 | B2 | 6/2008 | Cummings |
| 7,510,572 | B2 | 3/2009 | Gabbay |
| 7,621,948 | B2 | 11/2009 | Herrmann et al. |

(Continued)

FOREIGN PATENT DOCUMENTS

| | | |
|---|---|---|
| JP | 2008-523922 | 7/2008 |
| JP | 2012-521854 | 9/2012 |

(Continued)

OTHER PUBLICATIONS

PCT Written Opinion for PCT/US19/12406, published Jul. 2019, 17 pages.

*Primary Examiner* — Katrina M Stransky
(74) *Attorney, Agent, or Firm* — Nathan S. Smith; Morgan, Lewis & Bockius LLP

(57) ABSTRACT

The present disclosure relates to heart valve prostheses, delivery devices, actuation handles, and other improved devices and methods that facilitate delivery of a heart valve prosthesis to a defective native valve structure in a patient, such as the aortic valve.

21 Claims, 17 Drawing Sheets

(56) References Cited

U.S. PATENT DOCUMENTS

| | | |
|---|---|---|
| 7,789,909 B2 | 9/2010 | Andersen et al. |
| 7,803,185 B2 | 9/2010 | Gabbay |
| 7,824,443 B2 | 11/2010 | Salahieh et al. |
| 8,052,750 B2 | 11/2011 | Tuval et al. |
| 8,105,375 B2 | 1/2012 | Navia et al. |
| 8,313,525 B2 | 11/2012 | Tuval et al. |
| 9,554,903 B2 | 1/2017 | Rowe et al. |
| 2002/0032481 A1 | 3/2002 | Gabbay |
| 2003/0036791 A1 | 2/2003 | Bonhoeffer et al. |
| 2003/0040792 A1 | 2/2003 | Gabbay |
| 2003/0149478 A1 | 8/2003 | Figulla et al. |
| 2004/0260394 A1 | 12/2004 | Douk et al. |
| 2005/0137688 A1 | 6/2005 | Salahieh et al. |
| 2005/0137689 A1 | 6/2005 | Salahieh et al. |
| 2005/0251251 A1 | 11/2005 | Cribier |
| 2006/0173524 A1 | 8/2006 | Salahieh et al. |
| 2006/0217802 A1 | 9/2006 | Ruiz et al. |
| 2006/0259134 A1* | 11/2006 | Schwammenthal ...... A61F 2/24 623/2.11 |
| 2006/0259135 A1 | 11/2006 | Navia et al. |
| 2007/0016286 A1 | 1/2007 | Herrmann et al. |
| 2007/0027533 A1 | 2/2007 | Douk |
| 2007/0027534 A1 | 2/2007 | Bergheim et al. |
| 2007/0100440 A1 | 5/2007 | Figulla et al. |
| 2007/0244552 A1 | 10/2007 | Salahieh et al. |
| 2007/0250151 A1 | 10/2007 | Pereira |
| 2007/0250161 A1 | 10/2007 | Dolan |
| 2007/0260225 A1 | 11/2007 | Sakakine |
| 2008/0071361 A1 | 3/2008 | Tuval et al. |
| 2008/0071363 A1 | 3/2008 | Tuval et al. |
| 2008/0082166 A1 | 4/2008 | Styrc et al. |
| 2008/0177381 A1 | 7/2008 | Navia et al. |
| 2009/0054968 A1 | 2/2009 | Bonhoeffer et al. |
| 2009/0054976 A1 | 2/2009 | Tuval et al. |
| 2009/0132035 A1 | 5/2009 | Roth et al. |
| 2009/0192585 A1 | 7/2009 | Bloom et al. |
| 2009/0216310 A1 | 8/2009 | Straubinger et al. |
| 2009/0240320 A1 | 9/2009 | Tuval et al. |
| 2009/0275934 A1 | 11/2009 | Baxter et al. |
| 2009/0287299 A1 | 11/2009 | Tabor et al. |
| 2010/0100167 A1* | 4/2010 | Bortlein ...... A61F 2/95 623/1.11 |
| 2010/0249915 A1 | 9/2010 | Zhang |
| 2010/0249916 A1 | 9/2010 | Zhang |
| 2010/0256751 A1 | 10/2010 | Rowe et al. |
| 2010/0274088 A1 | 10/2010 | West et al. |
| 2010/0286768 A1* | 11/2010 | Alkhatib ...... A61F 2/2418 623/2.11 |
| 2011/0202128 A1* | 8/2011 | Duffy ...... A61F 2/2436 623/2.11 |
| 2011/0264202 A1 | 10/2011 | Murray, III |
| 2013/0211508 A1 | 8/2013 | Lane et al. |
| 2013/0231735 A1* | 9/2013 | Deem ...... A61F 2/243 623/2.11 |
| 2013/0261737 A1* | 10/2013 | Costello ...... A61F 2/2436 623/2.11 |
| 2014/0200649 A1* | 7/2014 | Essinger ...... A61F 2/9517 623/1.12 |
| 2015/0148894 A1* | 5/2015 | Damm ...... A61M 25/0147 623/2.11 |
| 2015/0320556 A1 | 11/2015 | Levi et al. |
| 2016/0015512 A1 | 1/2016 | Zhang et al. |
| 2016/0262884 A1* | 9/2016 | Lombardi ...... A61F 2/2436 |
| 2017/0128203 A1 | 5/2017 | Zhang et al. |
| 2017/0165062 A1 | 6/2017 | Rothstein |
| 2018/0021129 A1 | 1/2018 | Peterson et al. |
| 2020/0253731 A1 | 8/2020 | Manash |

FOREIGN PATENT DOCUMENTS

| | | |
|---|---|---|
| JP | 2016-516492 | 6/2016 |
| WO | WO 2004/019825 | 3/2004 |
| WO | WO 2005/002466 | 1/2005 |
| WO | WO 2009/155561 | 12/2009 |
| WO | WO 2010/121076 | 10/2010 |
| WO | WO 2012/095455 | 7/2012 |
| WO | WO 2014/153152 | 9/2014 |
| WO | WO 2017/121194 | 7/2017 |
| WO | WO 2017/195125 | 11/2017 |

* cited by examiner

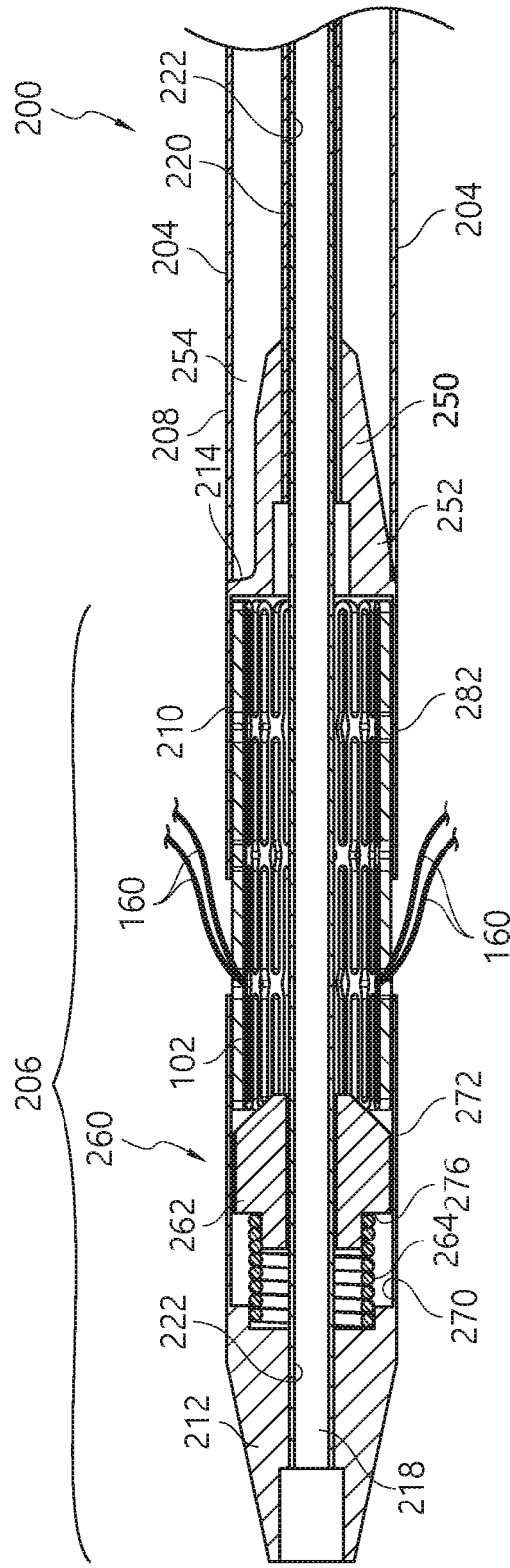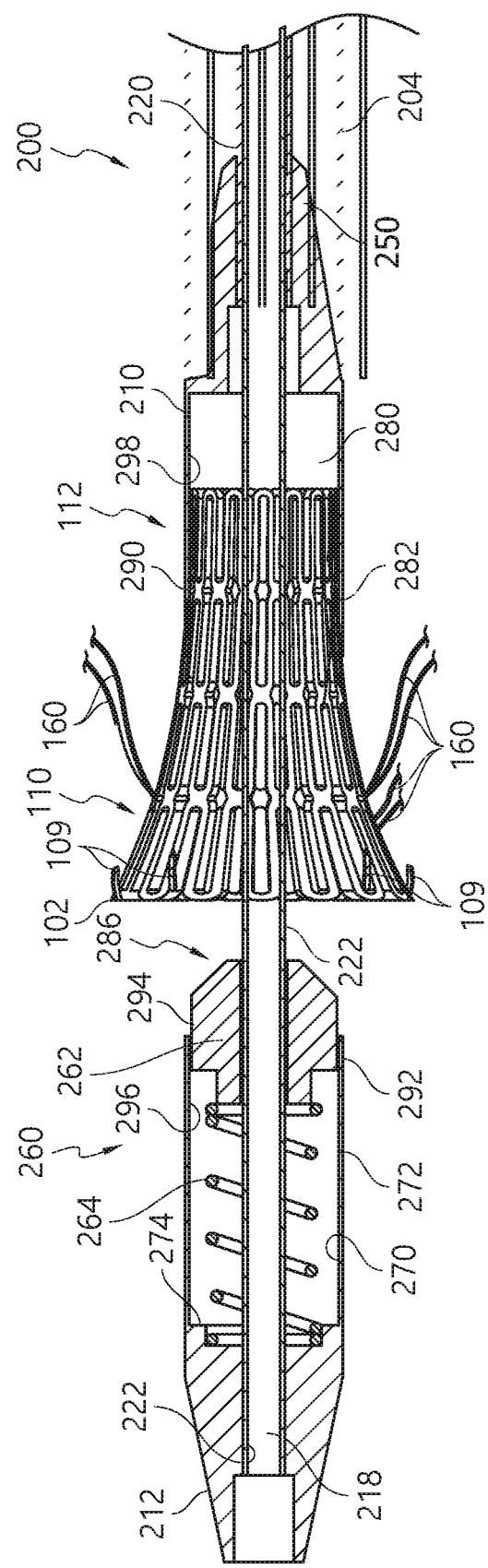

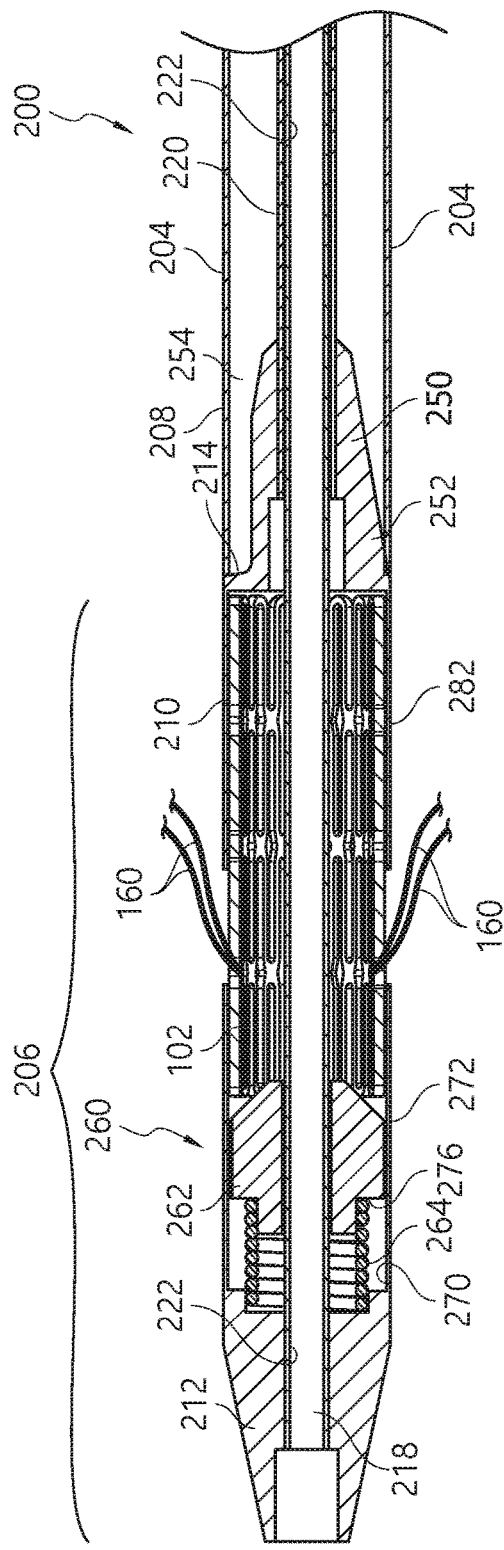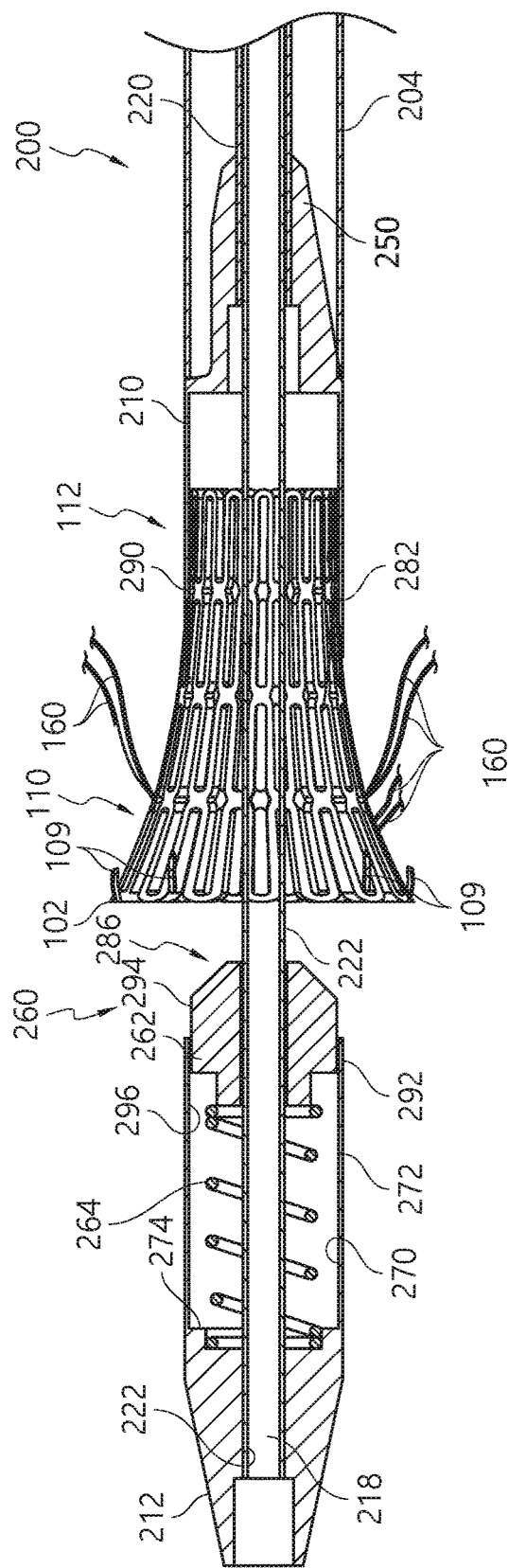
FIG. 7A
FIG. 7B

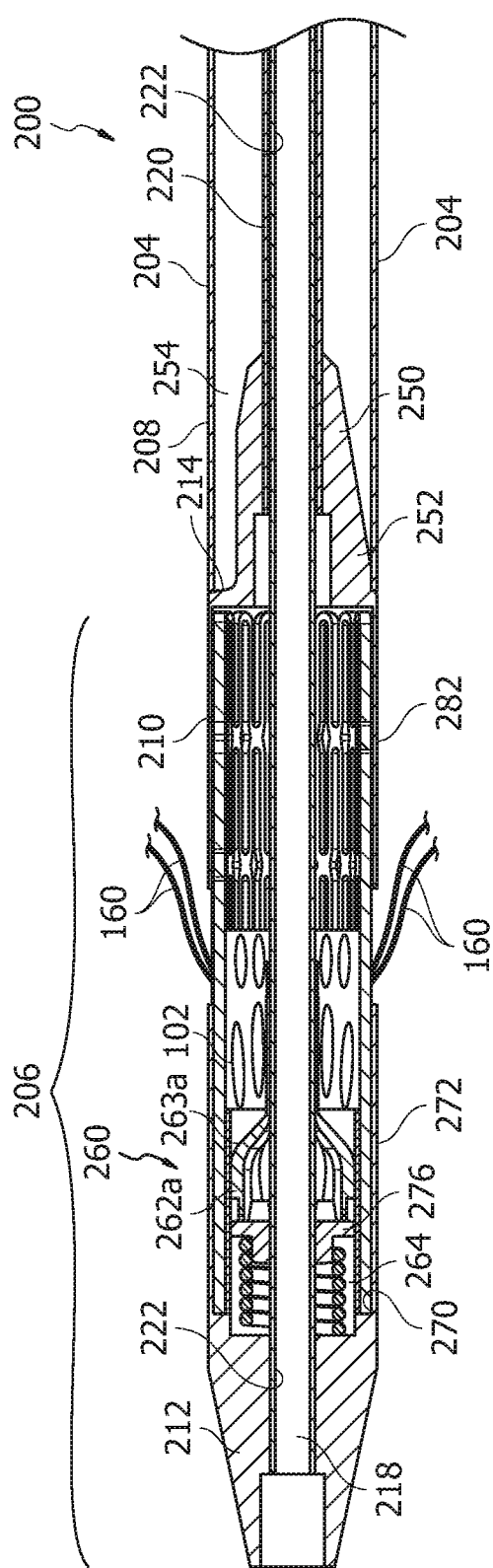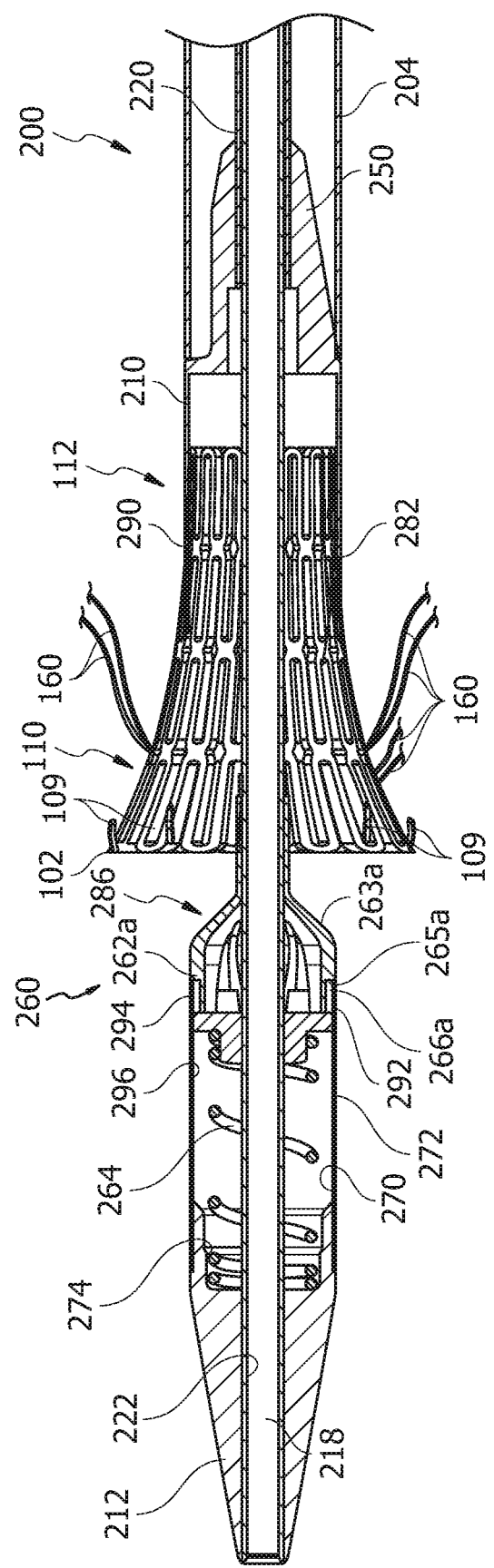

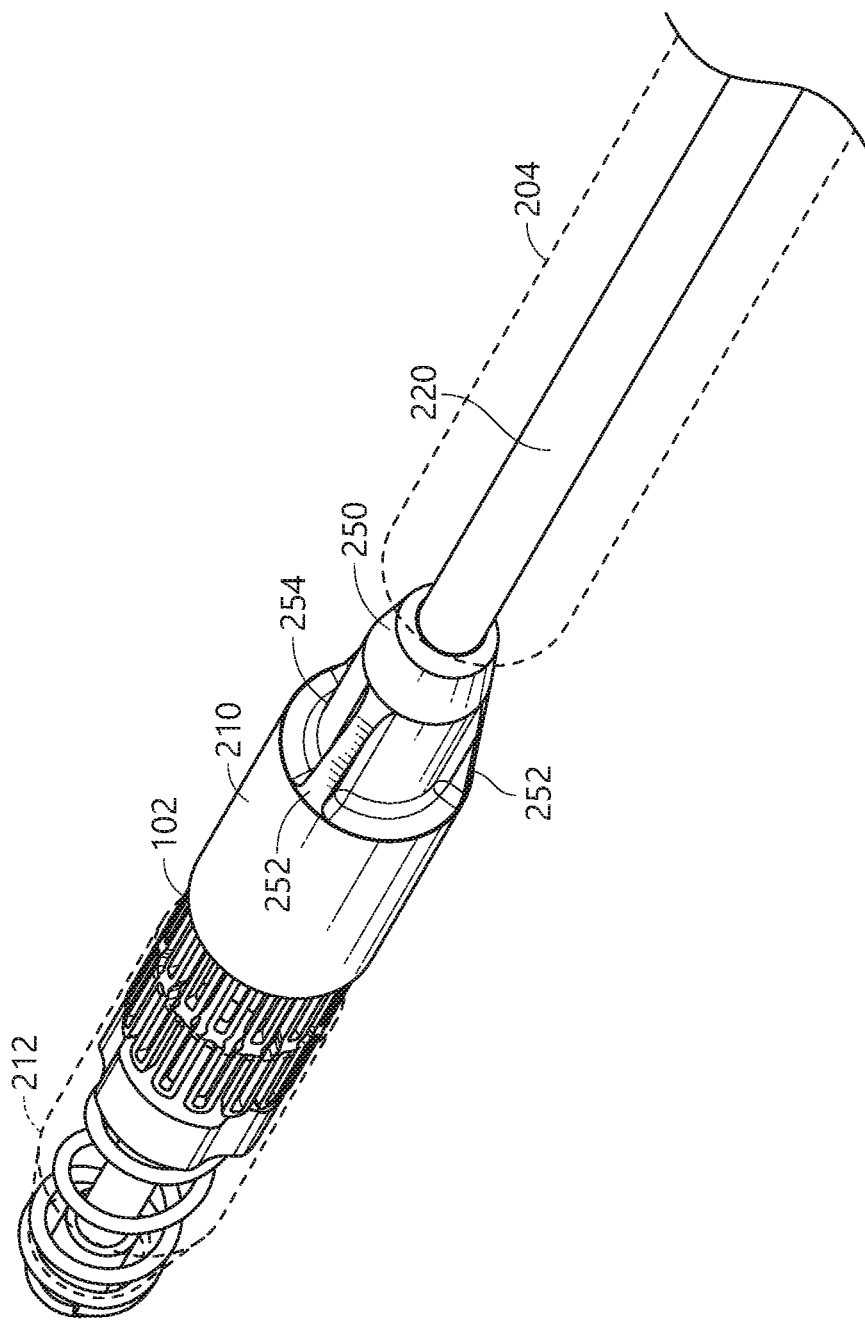

HEART VALVE PROSTHESIS DELIVERY SYSTEM

CROSS-REFERENCE TO RELATED APPLICATIONS

The present application claims the benefit of and priority to U.S. Provisional Application No. 62/614,489, filed on Jan. 7, 2018, U.S. Provisional Application No. 62/756,556, filed on Nov. 6, 2018, and U.S. Provisional Application No. 62/781,537, filed on Dec. 18, 2018, the entireties of each of which are incorporated herein by reference.

TECHNICAL FIELD

The present disclosure relates to devices and methods for the percutaneous delivery and implantation of a cardiac valve prosthesis. The valve prosthesis can be delivered in a compressed state within a sheath to the defective native valve and released in situ.

BACKGROUND

Prosthetic heart valves are used to replace damaged or diseased heart valves. In vertebrate animals, the heart is a muscular organ with four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is more common since they reside in the left side of the heart where pressures are the greatest.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open-heart surgery is particularly invasive and involves a lengthy and difficult recovery period.

The foregoing examples of the related art and limitations related therewith are intended to be illustrative and not exclusive. Other limitations of the related art will become apparent to those of skill in the art upon a reading of the specification and a study of the drawings.

SUMMARY

The present disclosure relates to heart valve prostheses, delivery devices, and actuation handles that can facilitate delivery of a heart valve prosthesis to a defective native valve structure in a patient, such as the aortic valve. In some embodiments, the delivery can be performed using a transcatheter approach.

The delivery devices and actuation handles can enable a clinician to more easily maneuver and advance the delivery device through blood vessels leading to the heart, as well as through tortuosities of such vessels, using a transvascular approach, such as a transfemoral approach. Indeed, some embodiments disclosed herein enable components of the heart valve prosthesis to be advanced in tandem, as an axially displaced unit (with or without partial or full overlapping between the components), while still being movably connected, movably attached, flexibly connected, displaceably connected, linked, or coupled to each other, thereby minimizing a passing profile or cross section of the delivery device. Optionally, the distance from which the components of the heart valve prosthesis may be serially displaced may be variable, such that various components are adjacent or potentially inches or feet away. Further, the interconnection of components of the heart valve prosthesis can allow different degrees of motion and can be set into an engaged or retained position that provides a limited range of motion. In some embodiments, the engaged position can also provide a preset relative positioning of the components of the heart valve prosthesis to facilitate proper placement and release of the heart valve prosthesis. Additionally some embodiments can provide a clinician with a high degree of control and enhance the maneuverability of the heart valve prosthesis when implanting the heart valve prosthesis at the target location.

In accordance with some embodiments, a procedure is provided for a transcatheter aortic valve implantation (TAVI) and/or a transcatheter aortic valve replacement (TAVR). For example, in the TAVI procedure, a clinician can anchor the anchoring component of the heart valve prosthesis relative to the aortic valve annulus to guide the placement of the prosthetic leaflet structure. The valve prosthesis can comprise prosthetic leaflets, an anchoring component, a valve frame component, and a tethering component, which allows the anchoring component and the frame component to be placed serially in a delivery device in order to reduce the overall crossing profile of the delivery device. The tethering component can be coupled to the anchoring component and the frame component to permit a range of motion and in some embodiments, to restrict other motion. The tethering component can be slidable relative to the anchoring component between a released position and a retained position. In the retained position, the tethering component can allow relative movement of the valve frame component and a preset or predetermined position which the valve frame component is optimally located relative to the anchoring component, which can facilitate placement and release of the valve prosthesis.

For example, in some embodiments, the interconnection can be implemented using a novel approach of looping the tethering component around "U-shaped" members of the anchoring component. The tethering component can slide along the anchoring component until reaching the end of the travel on the anchoring component. The clinician can exert tension on the tethering component until the tethering component is seated in the engagement area. This action can ratchet the tethering component and engage it to the engagement area of the anchoring component. Thereafter, the tethering component establishes a fixed range of longitudinal travel of the valve frame component relative to the anchoring component, and subsequently a proper position of the valve frame component in the anatomy, based only on the clinician placing the anchoring component into the aortic sinus region (the clinician can see under fluoroscopy and can "feel" the placement).

Thus, some embodiments disclosed herein advantageously provide a delivery device that has a reduced passing profile or cross section, thereby enabling delivery of a heart valve prosthesis in a safer, less invasive manner than traditional approaches. As such, open-heart surgery can be avoided because the heart valve prosthesis can be advanced to the heart using a catheter via an access point in the blood vessel, such as the femoral artery. This provides enormous benefits to patients, including less trauma to the patient, greater ease of recovery, and potentially fewer surgical risks, to name a few.

Further, although the in-series arrangement of the anchoring component and the valve frame component overcomes the challenge of creating a low-profile delivery device, the advantageous arrangement of the interconnection overcomes yet another critical challenge: how to optimally position the valve prosthesis within the native valve structure and to reliably anchor it in place. Indeed, some embodiments disclosed herein address this challenge and teach structures and methods for using a tethering component to operatively couple the anchoring component to the valve frame component in a delivery device.

The delivery device can comprise a proximal sheath that can house at least a portion of the anchoring component and a distal carrier assembly that can house at least a portion of the valve frame component. The tethering component can extend between the anchoring component and the valve frame component when the valve prosthesis is loaded onto the delivery device. The valve prosthesis can be released from the delivery device in a component-by-component manner that allows the clinician to maneuver and position the anchoring component first, followed by the valve frame component.

In some embodiments, the anchoring component can be coupled to an engagement member or grasper of the delivery device that allows the clinician to push or pull the anchoring component. The grasper can be released from engagement with the anchoring component when the anchoring component is properly seated relative to the native valve annulus.

In addition, in some embodiments, the distal carrier assembly of the delivery device can comprise two components or be referred to as a two-part nose cone assembly. In accordance with some embodiments is the realization that if a single tubular member or nose cone is used to sheath most of the valve frame component, various problems can arise due to the expansive force and corresponding compressive force required to maintain the valve frame component in its compressed configuration during delivery to a target valve structure. Because the delivery device can be quite long (for example, in some embodiments, up to about 4 to 6 feet or more, although the length can be less than 4, 3, or 2 feet), these forces can create a much stiffer distal section of the delivery device. Further, these forces can require a high degree of longitudinal force to release the valve frame component due to the high frictional forces due to the radial force of the valve implant.

Thus, the radial and frictional forces of such configurations can cause problems of matching handle actuation and make precise positioning of the distal end of the delivery device quite difficult. For example, the friction tends to be a variable friction that makes it difficult for a clinician to position the components of the valve prosthesis relative to each other, which can lead to unpredictable and/or imprecise component positioning or deployment. Thus, some embodiments herein include the realization that by separating the distal carrier or nose cone assembly into two components (such as a proximal and distal enclosure), the components can cover less surface area of the valve frame component, thus reducing the radial forces exerted on a single component and the resultant friction that would need to be overcome in order to actuate or release the valve frame component. As such, the problems associated with a single tubular member are much more manageable.

Additionally, in some embodiments, a two-part distal carrier assembly can also enable the clinician to release the valve frame component in an advantageous sequence. For example, during testing and development of the valve prostheses, deployment systems, and handle actuators disclosed herein, some embodiments demonstrate advantageous characteristics by permitting a distal end portion of the valve frame component to open first, before a proximal end portion of the valve frame component is released. In some embodiments, the valve frame component can have one or more anchors at its distal end portion that can supplement the outward expansive force (due to self-expansion of the valve frame component) and its resultant frictional engagement. By opening the distal end portion first (by actuation of distal nose cone or enclosure), the distal end portion can "flower" out and engage with the native valve structure to secure a longitudinal position of the valve frame component relative to the native valve structure. Thereafter, the self-expanding radial outward force of the valve frame component can cause the proximal end portion of the valve frame component to become disengaged and released from the proximal nose cone or enclosure.

Some embodiments can also provide self-aligning features to allow the components of the delivery assembly to be moved from a releasing state (where the components of the valve prosthesis are released from engagement with the delivery assembly) to a nested or stowed state in which outer surfaces of portions of the delivery assembly are aligned or in an abutting position at a seam. This alignment, abutment, or positioning can provide a smoother outer profile that can reduce the likelihood of having the delivery assembly snag or become entangled with the prosthetic valve after being released or with other vasculature as the delivery assembly is retrieved from the patient's vasculature.

For example, in some embodiments, the distal carrier or nose cone assembly can include an internal plunger or piston mechanism. The plunger mechanism can be compressed when the valve frame component is loaded into the delivery device. As the valve frame component is released, a spring of the plunger mechanism can push a plunger head to a predetermined position relative to the distal carrier assembly. In accordance with some embodiments, in the predetermined position, the plunger head can be exposed partially from the distal enclosure and be configured to engage with the proximal enclosure to align the proximal and distal enclosures relative to each other in an abutting relationship. The plunger head can therefore engage with both the proximal and distal enclosures to reduce the likelihood of catching or snagging of the delivery device with the prosthetic valve or other vasculature during retrieval of the delivery device. Additionally, such features can also aid in proximal retraction of the delivery device into an introducer sheath. Moreover, the plunger head can also provide a proximal surface that can be in contact with the distal end portion of the valve frame component and not catch or snag with the intricate mesh of the valve frame component, thereby ensuring that the valve frame component can flower open without catching on the delivery device. Accordingly, some embodiments can include one or more of these advantageous features that address the problem of having the valve prosthesis and/or the delivery device catch or snag on each other or surrounding anatomy.

Furthermore, due to the reduced cross-sectional profile of the delivery device, retrograde delivery of a valve prosthesis through the blood vessel (such as femoral artery in a transfemoral retrograde approach) can be possible with reduced risk of trauma to the surrounding vasculature. For example, retrograde delivery of the valve prosthesis through the femoral artery has been associated with aortofemoral artery injury and/or rupture, and carries a potential risk of stroke as the delivery involves crossing the aortic arch. However, the various features and advantages achieved using some embodiments disclosed herein provide a valve prosthesis and delivery device that minimizes damage along the delivery path of device while also minimizing the invasive nature of the implantation procedure.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded or omitted from any embodiment of the present disclosure. Additional aspects and advantages of the present disclosure are set forth in the following description and claims, particularly when considered in conjunction with the accompanying examples and drawings.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Certain features of valve prostheses, delivery devices, actuation handles, other devices, systems, and methods which can be implemented with the valve prostheses, delivery devices, actuation handles, other devices, systems, and methods discussed in the present disclosure, can implement features of and/or be used in combination with other features of valve prostheses, delivery devices, actuation handles, other devices, systems, and methods described for example in International Application No. PCT/US2019/012406, entitled HEART VALVE PROSTHESIS, filed on Jan. 4, 2019, by Ji Zhang, Brandon G. Walsh, Cheng Yong Yang, Jinhua Zhu, and Dennis Michael McMahon, and in International Application No. PCT/US2019/012408, entitled PROSTHETIC HEART VALVE DELIVERY SYSTEM, filed on Jan. 4, 2019, by Ji Zhang, Brandon G. Walsh, and Cheng Yong Yang, the entirety of each of which is incorporated herein by reference.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 5A and 5B are side cross-sectional views illustrating operation of a distal carrier assembly of the valve delivery device of FIG. 3 with a nose cone protector, according to some embodiments.

FIGS. 7A-7D are side and end cross-sectional views illustrating aspects and operation of a distal carrier assembly and a proximal enclosure of a delivery device, according to some embodiments.

FIGS. 8B-8F are side cross-sectional views illustrating operation of a distal carrier assembly of the delivery device with the nose cone protector of FIG. 8A, according to some embodiments.

FIGS. 10A and 10B are perspective views illustrating a structure of a proximal enclosure of the delivery device of FIG. 6, according to some embodiments.

DETAILED DESCRIPTION

Figure 1:
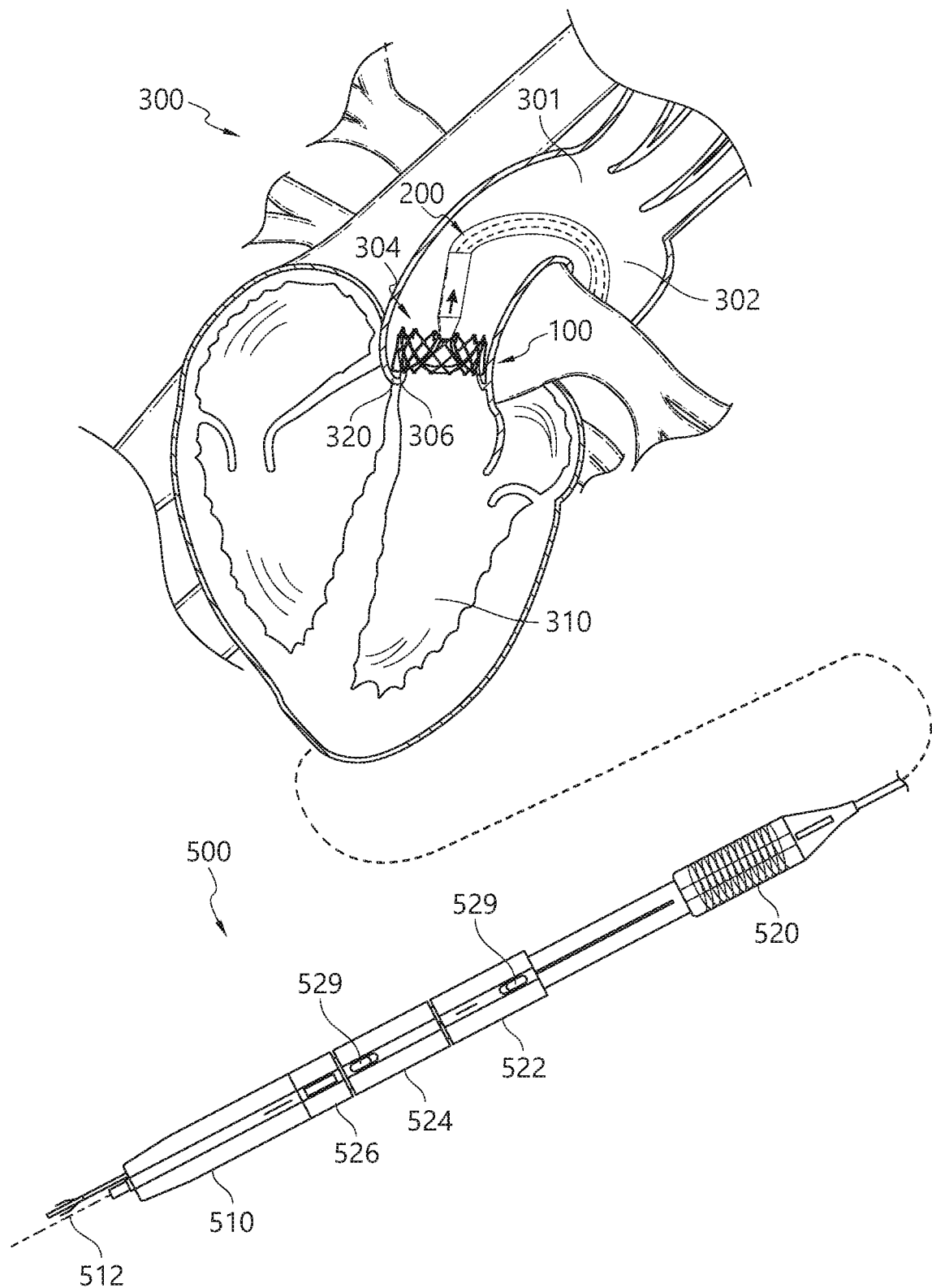
FIG. 1 illustrates delivery of a valve prosthesis using a valve delivery device in a transfemoral retrograde approach, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present disclosure sets forth specific details of various embodiments, it will be appreciated that the description is illustrative only and should not be construed in any way as limiting. Additionally, it is contemplated that although particular embodiments of the present disclosure may be disclosed or shown in the context of aortic valve prostheses, such embodiments may be used in other cardiac valve prosthesis applications. Furthermore, various applications of such embodiments and modifications thereto, which may occur to those who are skilled in the art, are also encompassed by the general concepts described herein.

Various embodiments will now be described more fully hereinafter. Such embodiments may, however, be embodied in many different forms and should not be construed as limited to the embodiments set forth herein; rather, these embodiments are provided so that this disclosure will be thorough and complete, and will fully convey its scope to those skilled in the art. Thus, one or more features shown or otherwise disclosed in an embodiment herein may be interchangeably used or incorporated into another embodiment that may not expressly show or disclose such feature(s). Further, one or more features shown or otherwise disclosed for an embodiment herein may be excluded from such embodiment, unless expressly indicated, using skill in the art.

As with all cardiac valves, a healthy aortic valve will open to allow blood flow and close to prevent backflow of blood. However, disease and dysfunction of the valve can result in regurgitation or decreased blood flow (stenosis). In such cases, a replacement aortic valve prosthesis must be used to perform the functions of a healthy aortic valve.

Minimally invasive surgical techniques are evolving, where a valve prosthesis can be introduced into a patient using a catheter that is introduced via a small incision that provides access to, for example, a femoral artery or directly to the heart. These implantation techniques have shown promising results in providing treatment options for patients who are poor open surgical candidates. Nevertheless, challenges still remain in such catheter-based delivery of prosthetic valves.

For example, in according with an aspect of at least one embodiment disclosed herein is the realization that advancing a conventional tubular delivery device through a vessel exerts stress against the vessel walls and carries the risk of damaging the vessel walls. Further, in according with an aspect of at least one embodiment disclosed herein is the realization that transcatheter prosthetic valves may not be able to treat patients with aortic regurgitation. Additionally, in according with an aspect of at least one embodiment disclosed herein is the realization that conventional prosthetic valves may be difficult to position, may require rapid ventricular pacing, and may have limited expansion. Accordingly, implantation and use of conventional prosthetic valves may result in complications, such as vascular damage, moderate to severe paravalvular leakage, valve thrombosis/migration, coronary artery blockage, and excessive stress due to excessive radial force.

The present disclosure describes various aspects of heart valve prostheses that can be delivered to a defective heart valve in a patient. The valve prostheses can comprise at least one valve anchor or clasper, which is movably connected, movably attached, flexibly connected, displaceably connected, linked, or coupled to a radially-expandable valve support or frame. The valve frame can comprise prosthetic valve leaflets or cusps and provide the functionality of the native heart valve. Certain features of valve prostheses, which can be implemented with the prostheses discussed in the present disclosure, are also further described for example, in U.S. Pat. No. 8,366,768, the entirety of which is incorporated herein by reference.

Thus, the present disclosure provides a variety of features that can be optionally incorporated or excluded from any of the embodiments explicitly discussed or illustrated herein. These modifications and combinations of features can be performed by a person of skill to achieve advantages and benefits discussed herein. Further, certain modifications or combinations are indicated or suggested herein, but it is contemplated that a person skill can implement or exclude certain aspects or features disclosed herein in developing a suitable embodiment or implementation of these teachings. Advantageously, various embodiments described herein allow for treating patients with aortic regurgitation, permit precise axial, angular, and radial positioning of the valve prosthesis, minimize valve migration and paravalvular leakage while avoiding damage to the valve annulus, minimize the need for a pacemaker, and decrease the likelihood of blocking the coronary artery.

Some of these features and benefits of the heart valve prosthesis are illustrated with respect to FIGS. 1-5. FIG. 1 illustrates the use of the delivery device 200 in a human heart 300. The heart 300 can comprise an aorta 301 having an aortic arch 302 and an aortic valve 304. The aorta valve 304 can comprise a plurality of native valve leaflets 306 and separate the aorta 301 from the left ventricle 310. In accordance with some embodiments, the delivery device 200 can be advanced retrograde through the aorta 301 until reaching and being positioned through the native valve leaflets 306 of the aortic valve 304.

Figure 2:
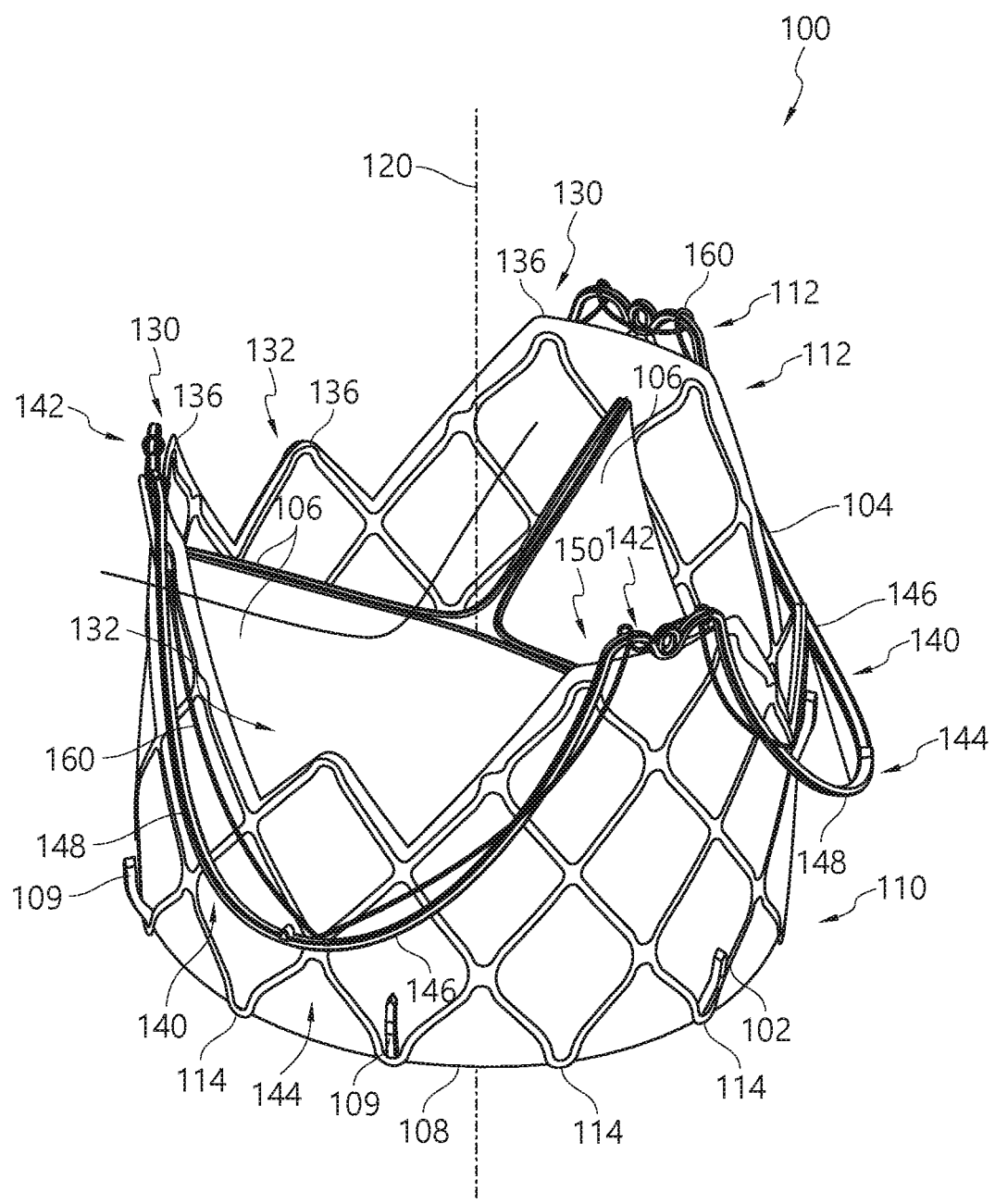
FIG. 2 shows a valve prosthesis, according to some embodiments.

With reference to FIGS. 1 and 2, during delivery of the valve prosthesis 100 to the native valve site, the valve anchor 104 and the support frame 102 can be positioned in tandem, as an axially displaced unit (with or without partial or full overlapping between the anchor and the frame) along the longitudinal axis of the delivery device 200. This configuration, as opposed to a concentric arrangement, can allow a more radially compact configuration of the components of the valve prosthesis 100, creating a much smaller cross-section and facilitating a catheter-based delivery. This can improve the flexibility of the delivery device 200, enabling the delivery device 200 to be advanced over a guidewire through the tortuous geometries of the circulatory system, and in particular, the aortic arch 302. Indeed, even with guidewire-directed delivery devices, the aortic arch 302 represents a difficult obstacle due to its sudden and high-degree of curvature. Often, this is a limiting constraint for some surgeries or delivery devices. However, in accordance with the various benefits and advantages of some embodiments disclosed herein, as illustrated in FIG. 1, the delivery device 200 can be advanced over the aortic arch 302 to a target location in the region of the aortic valve 304.

As shown in FIG. 1, once the valve anchor 104 is in the desired position, the support frame 102 can be released from the distal carrier assembly and expanded into apposition with the native valve leaflets 306 and the internal aspects of the valve anchor 104, thus sandwiching the native valve leaflets 306 between the support frame 102 and the valve anchor 104. Advantageously, by sandwiching the native valve leaflets 306 between the support frame and the valve anchor, the valve prosthesis 100 can have reduced reliance on radial force retention. Further, by sandwiching the native valve leaflets 306 between the support frame and the valve anchor, the likelihood of the native valve leaflets 306 blocking the opening of the coronary artery is reduced, which may be beneficial for patients with low coronary ostia distance, and in patients with an existing valve prosthesis, who may need a new valve prosthesis inside the existing valve prosthesis (valve-in-valve application). The support frame and the valve anchor can thus expand into contact with the aortic valve 304, exerting a chronic outward force against the native valve leaflets 306 and aortic valve annulus 320. Thereafter, the prosthetic valve leaflets of the prosthesis 100 can begin to function in the manner desired and provide the same operation as a native valve.

According to some embodiments, the present disclosure also provides a handle actuator that can be used to control the operation of the presently disclosed delivery device and allow a clinician to reliably and accurately control the delivery of the valve prosthesis. FIG. 1 illustrates features and operation of the handle actuator, according to some embodiments, for delivering a valve prosthesis using a handle actuator 500.

FIG. 1 illustrates the handle actuator 500, which can control one or more functions of a delivery device (e.g., the delivery device 200 discussed herein) for delivering of a valve prosthesis (e.g., the heart valve prosthesis 100 discussed herein). The handle actuator 500 can comprise a plurality of actuators or movable elements, such as knobs or buttons. The movable elements can permit a clinician to control one or more operations of the delivery device 200. The handle actuator 500 can comprise a control handle 510 having a longitudinal axis 512. The handle actuator 500 may be also referred to as a control unit. In some embodiments, the handle actuator 500 may be coupled to the second core member 222 (shown, e.g., in FIGS. 3 and 5). The control handle 510 can support the actuators and be held by the clinician during the procedure.

In some embodiments, as illustrated in FIG. 1, the handle actuator 500 can comprise a first movable element 520, a second movable element 522, a third movable element 524, and a fourth movable element 526. The first movable element 520 can be used to steer the delivery device 200, the second movable element 522 can be used to release the valve anchor, the third movable element 524 can be used to release nosecone or valve frame, and the fourth movable element 526 can be used as a nose cone toggle lock. The first movable element 520, the second movable element 522, the third movable element 524, and the fourth movable element 526 may be also referred to as the first control element 520, the second control element 522, the third control element 524, and the fourth control element 526.

Optionally, in some embodiments, one or more of the movable elements, such as the second movable element 522 and/or the third movable element 524, can include a button or slider safety switch 529 that prevent the unintentional rotation of the moveable elements. The safety switch 529 can be configured as resilient button or slider mechanisms that can be actuated to release a lock that provides resistance to rotational or translational movement of the respective movable element. In some embodiments, the movable elements can have a raised feature that provides a visual indication of rotation and facilitates tactile engagement and actuation by the clinician. Other features of the handle actuator 500 and methods for operating the handle actuator 500 are discussed and illustrated in FIGS. 13A-13H of U.S. Patent Application No. 62/781,537, filed on Dec. 18, 2018, the entirety of which is incorporated herein by reference.

Referring now to FIG. 2, a valve prosthesis 100 and components thereof are shown in various configurations. The valve prosthesis 100 can be delivered to a patient using a suitable delivery device, including embodiments of the delivery devices disclosed herein. The valve prosthesis 100 can comprise a support frame 102 and an anchoring component or valve anchor 104 to which the support frame 102 is movably connected, movably attached, flexibly connected, displaceably connected, linked, or coupled.

The valve prosthesis 100 can be configured such that components of the valve prosthesis 100 to be advanced in series while still being movably connected, movably attached, flexibly connected, displaceably connected, linked, or coupled to each other, thereby minimizing a passing profile or cross section of the delivery system. The interconnection of components of the valve prosthesis 100 can allow different degrees of motion and can be set into an engaged or retained position that provides a limited range of motion. In some embodiments, the engaged position can also provide a preset relative positioning of the components of the valve prosthesis 100 to facilitate proper placement and release of the valve prosthesis 100. Additionally, some embodiments can provide a clinician with a high degree of control and enhance the maneuverability of the valve prosthesis 100 when implanting the valve prosthesis 100 at the target location.

In some embodiments, the valve anchor 104 can be coupled to the support frame 102 when the support frame 102 is in the compact configuration prior to delivery and expansion. In some embodiments, the valve anchor 104 is not fixed to the support frame 102. Further, the valve anchor 104 can be separate from the support frame 102 or formed separately from and later coupled to the support frame 102. Thus, although a least a portion of the valve anchor 104, e.g., the anchoring leg, may be in contact with or otherwise reversibly attached or connected to the support frame 102, no part of the valve anchor 104 is fixed, e.g., welded or otherwise irreversibly adhered, to the support frame 102. Alternatively stated, the valve anchor 104, which may be in contact with or otherwise reversibly attached to the support frame 102, is not irreversibly fixed to the support frame 102.

Further, upon reaching the target location, the valve anchor 104 can be movably coupled to the support frame 102 in a manner that prevents the entire valve anchor 104 from being radially displaced from the support frame 102 when the valve anchor 104 is initially expanded. For example, portions of the valve anchor 104 can be radially displaced from the support frame during initial "landing" of the valve anchor 104 against the native valve structure at the target location. In some embodiments, the support frame 102 can be deployed or expanded within the native heart valve structure, and the valve anchor 104 can become sandwiched between the support frame and the native valve tissue, becoming at least partially, and possibly fully, immobilized. The valve anchor 104 can function to hold the expanded support frame 102 in place within the native valve structure.

Optionally, the support frame 102 may be referred to as a valve frame or valve support frame. FIG. 2 illustrates the support frame 102 aligned with and expanded within the valve anchor 104, in a configuration that is achieved when the prosthesis 100 is released and expanded within the native valve structure. The native valve structure includes the valve annulus or leaflets. This expanded configuration, serves to secure the valve prosthesis 100 within the native valve annulus by engaging the native valve structure. In some embodiments, the expanded configuration of the valve prosthesis 100 may reduce reliance on securing the valve prosthesis 100 with radial force exerted by the support frame 102 and the valve anchor 104 via the sandwiching or compression of the native valve leaflets between the support frame 102 and the valve anchor 104 of the valve prosthesis 100. Further, as discussed further herein, during implantation of the valve prosthesis 100, the support frame 102 and the valve anchor 104 can be movable relative to each other in expanded and/or compressed states in order to facilitate proper positioning of the prosthesis 100 relative to the native valve annulus and surrounding structures. Indeed, various advantages made possible by the prosthesis 100 and delivery device disclosed herein allow a clinician to achieve a higher degree of precision in placing the prosthesis 100, as well as making such increased precision easier to achieve.

Referring to FIG. 2, the support frame 102 can comprise an outer or external surface and defines a central orifice about a longitudinal axis 120. The longitudinal axis 120 corresponds to an inflow-outflow axis of the prosthesis 100. In some embodiments, the valve prosthesis 100 further comprises a plurality of prosthetic valve leaflets or cusps 106 that are coupled to the support frame 102. The support frame 102 can provide a structural support for the valve leaflets 106. The valve leaflets 106 can have surfaces defining a reversibly sealable opening for unidirectional flow of a liquid through the prosthesis 100. The prosthesis 100 can include three valve leaflets 106 for a tri-leaflet configuration.

As appreciated, mono-leaflet, bi-leaflet, and/or multi-leaflet configurations are also possible. For example, the valve leaflets can be coupled to the support frame 102 to span and control fluid flow through the lumen of the prosthesis 100. The prosthetic leaflets 106 can comprise one or more synthetic materials, engineered biological tissues, biological valvular leaflet tissues, pericardial tissues, cross-linked pericardial tissues, aortic root tissue, chemically or biologically processed/treated tissue, or combinations thereof. In some embodiments, the pericardial tissue is selected from but not limited to the group consisting of bovine, equine, porcine, ovine, human tissue, or combinations thereof.

Furthermore, in some embodiments, the valve prosthesis 100 can comprise a sealing component or membrane 108 that can be attached to an inside surface, an outside surface, and/or enclose the support frame 102, such as by being laminated onto inner and outer surfaces of the support frame 102. Thus, the valve leaflets 106 can be coupled to the support frame 102 and/or the membrane 108. In some embodiments, the membrane 108 can restrict blood flow in areas around the valve leaflets 106 so that blood flow occurs only between the valve leaflets 106 through the lumen of the prosthesis 100, as in a healthy native heart valve.

The support frame 102 and/or the valve anchor 104 can comprise a braided frame, a wire frame, or a laser-cut frame (e.g., laser-cut tubular mesh), as shown in FIG. 2. In some embodiments, the support frame 102 and/or the valve anchor 104 can comprise a shape-memory metal, which can change shape at a designated temperature or temperature range or by inducing stress. Alternatively, the self-expanding frames can include those having a spring-bias. The material from which either the support frame 102 and/or the valve anchor 104 is fabricated can allow the support frame 102 and/or the valve anchor 104 to automatically expand to its functional size and shape when deployed but also allows the support frame 102 and/or the valve anchor 104 to be radially compressed to a smaller profile for delivery through the patient's vasculature. Examples of suitable materials for self-expanding components described herein (e.g., support frames, valve anchors, locking members) include, but are not limited to, medical grade nickel titanium alloys, tantalum, platinum alloys, niobium alloys, cobalt alloys, alginate, or combinations thereof. Shape memory alloys having superelastic properties generally made from ratios of nickel and titanium, commonly known as Nitinol, are preferred materials. In some embodiments, self-expanding components described herein can include materials including, but not limited to shape memory plastics, polymers, and thermoplastic materials which are inert in the body. In an alternative embodiment, either the support frame 102 and/or the valve anchor 104 is not self-expanding, and may be expanded, for example, using a balloon catheter as is well known in the art. Examples of suitable materials for components described herein include, but are not limited to, stainless steel and titanium. Optionally, either the support frame 102 and/or the valve anchor 104 can comprise radiopaque materials to allow visualization under fluoroscopy or other imaging techniques.

Optionally, the support frame 102 can comprise one or more hooks 109 that can engage with tissue of the native valve annulus, the aortic root, or any other portion of the native valve when the support frame 102 is expanded within the native valve annulus. The hooks 109 can be engaged with the native valve annulus to secure the prosthesis 100 and mitigate any downstream or antegrade migration of the prosthesis 100 during operation.

The support frame 102 can comprise a first end portion 110 and a second end portion 112. The first end portion 110 can be positioned upstream of the second end portion 112 when the prosthesis 100 is released within the native valve annulus. As illustrated in FIG. 2, the first end portion 110 of the support frame 102 can be shaped as a generally flat end of a cylinder, where first apices 114 of the support frame 102 lie generally in a common plane, which can be oriented substantially perpendicular relative to a longitudinal axis 120 of the prosthesis 100. Further, the second end portion 112 can be shaped to include a series of peaks 130 and valleys 132, where second apices or minor peaks 136 of the support frame 102 collectively form contours of the peaks 130 and valleys 132. The peaks 130 and valleys 132 of the second end portion 112 can be positioned downstream of the first end portion 110 when the prosthesis is seated within the native valve annulus.

In accordance with some embodiments, the prosthetic leaflets 106 can be coupled relative to the support frame 102 at locations circumferentially aligned with the peaks 130 of the second end portion 112, as shown in FIG. 2. In some embodiments, the prosthetic leaflets 106 can be coupled to the membrane 108 using ultra-high molecular weight polyethylene sutures. This unique configuration can advantageously enable the prosthesis 100 to more fully approximate the native valve structures, permit a more natural blood flow without limiting or otherwise constraining movement of the valve leaflets 106, and more seamlessly integrate with surrounding architecture of the heart. In some embodiments, the prosthetic leaflets 106 can comprise features, including, but not limited to, planar features, flat features, three-dimensional features, Bézier curves, or other suitable shapes. Optionally, the prosthetic leaflets 106 can be shaped through fixation on a leaflet-shaped mandrel.

The valve anchor 104 can comprise at least one U-shaped member, valve clasper, sinus locator, valve positioner, or valve hanger 140 that extends about a longitudinal axis of the valve anchor 104. As illustrated in FIG. 2, the valve anchor 104 can comprise a plurality of lobes or U-shaped members 140, such as three U-shaped members 140, but can have fewer or more. In some embodiments, U-shaped members 140 can be configured to engage with or fit inside the posterior aortic sinus, the left aortic sinus, and the right aortic sinus of a native aortic valve. The U-shaped members 140 can each have a peak portion 142 and a base portion 144. The U-shaped members 140 can each comprise first and second legs 146, 148. The first and second legs 146, 148 of the adjacent U-shaped members 140 can be interconnected at the peak portions 142 thereof. Further, the U-shaped members 140 can comprise shapes other than a U-shape, such as a wave-shape, V-shape, W-shape, or zig-zag. Optionally, multiple valve anchors 104 can each comprise one or more U-shaped members 140, wherein the multiple valve anchors 104 cooperatively engage with the aortic sinus to anchor the valve prosthesis as described herein.

The valve prosthesis 100 can include a link mechanism that interconnects the support frame 102 to the valve anchor 104. The link mechanism can comprise a single, continuous strand of material or multiple, independent strands of material that interconnects the support frame 102 to the valve anchor 104. Further, the link mechanism can attach in a sliding, engaged, or fixed manner to one or more locations on the support frame 102 and/or on the valve anchor 104.

In accordance with some embodiments, the valve anchor 104 may optionally define one or more engagement areas in one or more portions of the valve anchor 104, where a link mechanism may engage with the one or more engagement areas to restrict relative motion between the support frame 102 and the valve anchor 104.

For example, at the interconnection of the respective peak portions, the valve anchor 104 can define an engagement area 150. The engagement area 150 may also be referred to as a peak portion engagement area.

As illustrated in FIG. 2, the support frame 102 can be flexibly coupled to the valve anchor 104 via one or more tethering components or link mechanisms 160. The link mechanism 160 can be coupled to the support frame 102 and to the valve anchor 104, permitting relative movement between the support frame 102 and the valve anchor 104. However, the link mechanism 160 can be configured to limit relative movement between the support frame 102 and to the valve anchor 104. In some embodiments, the engagement area 150 of the valve anchor 104 can be used to further restrict relative motion of the support frame 102 with respect to the valve anchor 104 when the link mechanism 160 is engaged in the engagement area 150, as discussed herein.

The valve anchor 104 can thus be coupled to the support frame 102 to permit the valve anchor 104 to be moved axially or longitudinally relative to the support frame 102 while still remaining coupled to the support frame 102. This advantageous feature of some embodiments can allow a clinician to independently position the valve anchor 104 relative to the support frame 102. For example, in a transcatheter aortic valve replacement, the clinician can independently position the valve anchor 104 in order to fit the base portions 144 of the valve anchor 104 into the aortic sinus. Portions of the of aortic sinus may include the posterior aortic sinus, the left aortic sinus, and/or the right aortic sinus, of a native aortic valve. In some embodiments, the valve anchor 104 can rotate to be aligned in the respective aortic sinuses. In some embodiments, the interconnection of the valve anchor 104 to the support frame 102 can allow the valve anchor 104 to self-rotate to be aligned in the aortic sinus. Thereafter, with the valve anchor 104 "landed" in the respective aortic sinuses, the interconnection of the valve anchor 104 to the support frame 102 further enables the support frame 102 to translated along the longitudinal axis 120 of the valve prosthesis 100. In some embodiments, during the delivery procedure, the valve anchor 104 can be moved at least axially from a proximal position relative to the support frame 102, to a distal position relative to the support frame 102, or from either of such positions to a position in which the support frame 102 at least partially longitudinally overlaps with or is concentric within the valve anchor 104. A range of various positions are illustrated, for example, in FIGS. 11A-11F of U.S. Patent Application No. 62/781,537, filed on Dec. 18, 2018, the entirety of which is incorporated herein by reference.

For example, when the support frame 102 is nested within the valve anchor 104, as shown in FIG. 2, the base portions 144 of the valve anchor 104 can be longitudinally spaced apart from first end portion 110 of the support frame 102 along the longitudinal axis 120 at a distance which is about 10% to about 100%, about 25% to about 75%, about 33% to about 100%, about 33% to about 66%, about 25% to about 75%, about 50% to about 75%, or about 60% to about 70% of a length of the support frame 102. In some embodiments, the support frame 102 can be contained or otherwise fully overlapping the valve anchor 104. In some embodiments, the support frame 102 can have minimal or no overlap with the valve anchor 104. The support frame 102 can move along the longitudinal axis 120 to overlap the valve anchor 104 by about 10% to about 100%, about 25% to about 75%, about 33% to about 100%, about 33% to about 66%, about 25% to about 75%, or about 50% to about 75% of the length of the support frame 102. In accordance with some embodiments, the U-shaped members 140 of the valve anchor 104 can be in nested positions within the aortic sinuses, and the base portions 144 of the valve anchor 104 can be about longitudinally adjacent to, coplanar with, or spaced apart from the first end portion 110 of the support frame 102. For example, the valve anchor 104 can be in a nested position when at least one base portion 144 of the valve anchor 104 is in contact with or adjacent to the basal attachments of the native aortic valvar leaflets. Further, the first end portion 110 of the support frame 102 can be longitudinally adjacent to, coplanar with, or spaced apart from the native valve structure (or a virtual ring formed by the basal attachments of the native aortic valvar leaflets) or with the ventriculo-aortic junction.

The link mechanism 160 can allow rotational and longitudinal movement of the valve anchor 104 relative to the support frame 102. Thus, despite the presence of the link mechanism 160, the valve anchor 104 can move rotationally with respect to the support frame 102. Further, in some embodiments, the link mechanism 160 can be fixedly attached or coupled to the support frame 102 and fixedly or slidably attached to the valve anchor 104. When the support frame 102 is moved relative to the valve anchor 104, the link mechanism 160 can slide along the U-shaped members 140. In some embodiments, the U-shaped members 140 have a generally arcuate or convex shape (as illustrated with the U-shaped members of FIG. 2) that allows unrestricted movement of the link mechanism 160 along the geometry of the first and second legs 146, 148 of the U-shaped members 140. When the link mechanism 160 is allowed to slide along the first and second legs 146, 148 of the U-shaped members 140, the valve prosthesis 100 can be in a position referred to as a "slidable" state. In the slidable state, the range of longitudinal and/or rotational movement of the support frame 102 relative to the valve anchor 104 is variable and may be its greatest because the link mechanism 160 can move along the first and second legs 146, 148 of the U-shaped members 140.

In some embodiments, the link mechanism 160 can be fixedly attached or coupled to the support frame 102 and fixedly attached to the valve anchor 104. When the support frame 102 is moved relative to the valve anchor 104, the link mechanism 160 can stretch, flex, deform elastically and/or plastically. As the link mechanism 160 deforms, the range of longitudinal and/or rotational movement of the support frame 102 relative to the valve anchor 104 is variable as allowed by the deformation of the link mechanism 160.

In some embodiments, the link mechanism 160 can have multiple link members, where each link member is coupled to and intermittently spaced about a circumference of the support frame 102. Each link member may be slidably coupled to a respective one of the U-shaped members 140. Further, the link mechanism 160 can have multiple link members that are coupled together in an end-to-end manner. Moreover, the link mechanism 160 can have multiple link members that are individually coupled at one and to the support frame 102 and at another and to the valve anchor 104. Each of the link members can be slidable along the valve anchor 104, as disclosed similarly herein and not described again herein for brevity.

As noted above, however, the valve anchor 104 can also comprise engagement areas 150 that can engage with the link mechanism 160 in order to restrict relative motion between the support frame 102 and the valve anchor 104. The engagement areas 150 can include one or more local concavities or other geometric shapes that can engage or trap the link mechanism 160 once the link mechanism 160 passes into the engagement area 150. Various embodiments of engagement areas 150 can be used to permit the slidable link mechanism 160 to enter into the engagement area 150, but restrict the link mechanism 160 from exiting the engagement area 150, such as those disclosed in FIGS. 2A-2G of U.S. Patent Application No. 62/781,537, filed on Dec. 18, 2018, noted above.

Figure 3:
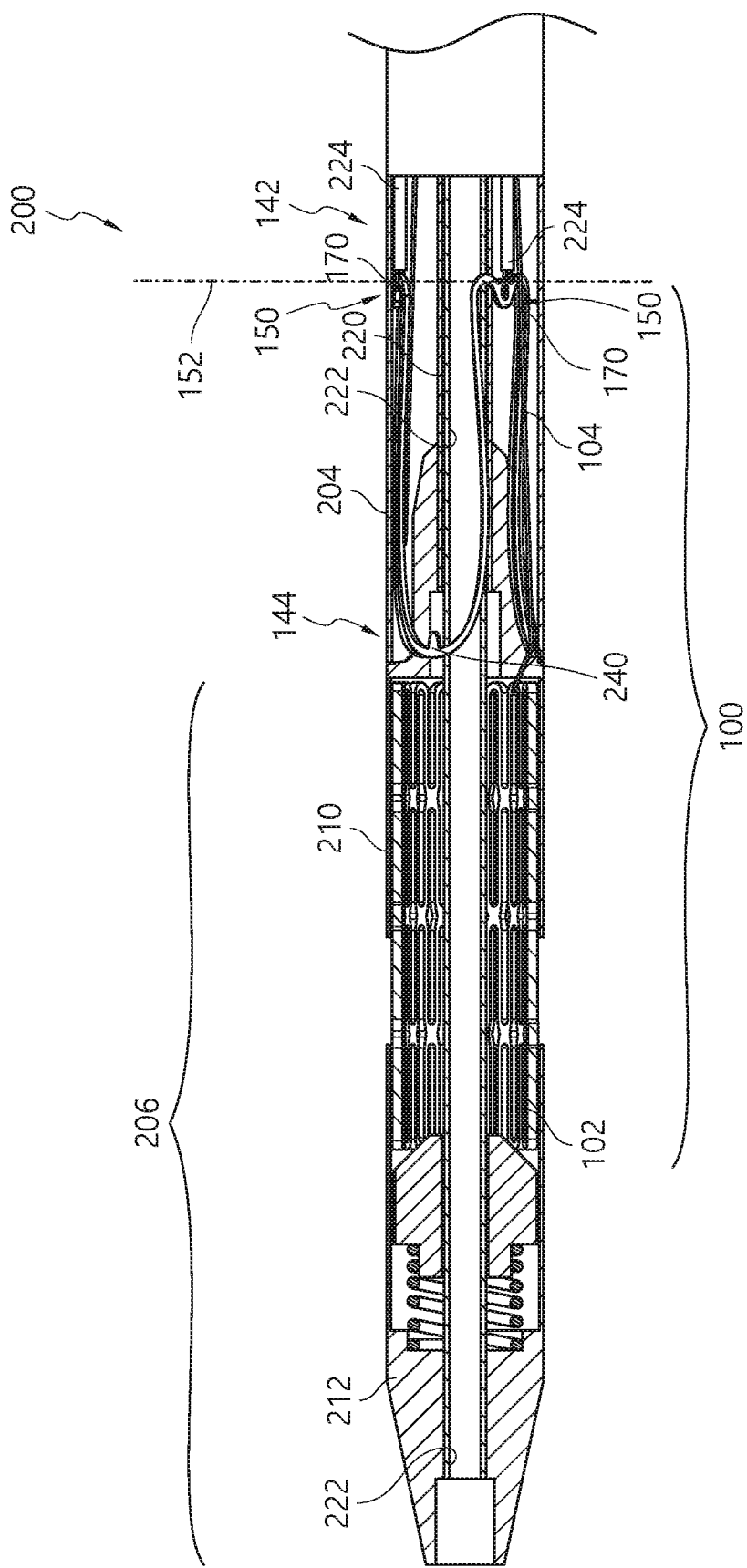
FIG. 3 is a side cross-sectional view of the valve prosthesis of FIG. 2 loaded onto a valve delivery device, according to some embodiments.

Referring now to FIG. 3, a side cross-sectional view is provided of the valve prosthesis 100 loaded onto the delivery device 200, according to some embodiments. Among the many features illustrated in FIG. 3, FIG. 3 shows that a proximal enclosure 210 of delivery device 200 can extend over both the valve anchor 104 and the support frame 102. Thus, in accordance with some embodiments, in the compressed or delivery configuration shown in FIG. 3, the link mechanism (not shown) can extend between the valve anchor 104 and the support frame 102 and be at least partially enclosed within the proximal enclosure 210 (depending on the attachment point of the link mechanism with the support frame 102 and the longitudinal extent of the proximal enclosure 210).

In addition, FIG. 3 illustrates that the valve anchor 104 can comprise a link motion limiter 240. The link motion limiter 240 can provide an enlarged profile of the wireframe structure of the valve anchor 104 so as to restrict or prevent motion of the link mechanism as the link mechanism slides along the U-shaped member of the valve anchor 104.

In alternative embodiments of the delivery device 200, the valve anchor 104 and the support frame 102 can both be enclosed within the proximal sheath component 204 prior to and during delivery prior to releasing the valve anchor 104. For example, in some embodiments, the valve anchor 104 can be distal to the support frame 102 wherein the valve anchor 104 is near the distal end of the proximal sheath component 204 and the support frame 102 can be approximately adjacent to the valve anchor 104 (in a serial configuration) and is proximal to the valve anchor 104. In some embodiments of the delivery device 200, the valve anchor 104 and the support frame 102 can both be enclosed within the proximal sheath component 204, with the support frame 102 near the distal end of the proximal sheath component 204 and the valve anchor 104 being approximately adjacent to the support frame 102 and proximal to the support frame 102.

Further, in alternative embodiments of the delivery device 200, the valve anchor 104 can be enclosed within the distal carrier assembly 206 and the support frame 102 can be enclosed within the proximal sheath component 204 prior to and during delivery of the valve prosthesis. For example, in some embodiments of the delivery device 200, both the valve anchor 104 and the support frame 102 can be enclosed within the distal carrier assembly 206 and the support frame 102 can be enclosed within the proximal sheath component 204 prior to and during delivery of the valve prosthesis. In this configuration, the valve anchor 104 and the support frame 102 can be approximately adjacent to one another (in a serial configuration) and the valve anchor 104 can be positioned proximal to the support frame 102. Other details of delivery devices and prostheses are provided in U.S. Patent Application No. 62/781,537, noted above and incorporated herein by reference.

In addition, FIG. 3 illustrates that an anchor retention component 170 can be used to engage the engagement areas 150 of the valve anchor 104 with the control member or a grasper 224 to facilitate movement and control of the positioning of the valve anchor 104 during delivery. As discussed with regard to FIGS. 7G-7I of U.S. Patent Application No. 62/781,537, noted above, this engagement can maintain the engagement areas 150 in a common plane 152, oriented generally perpendicular relative to the longitudinal axis of the delivery device 200.

Figure 4:
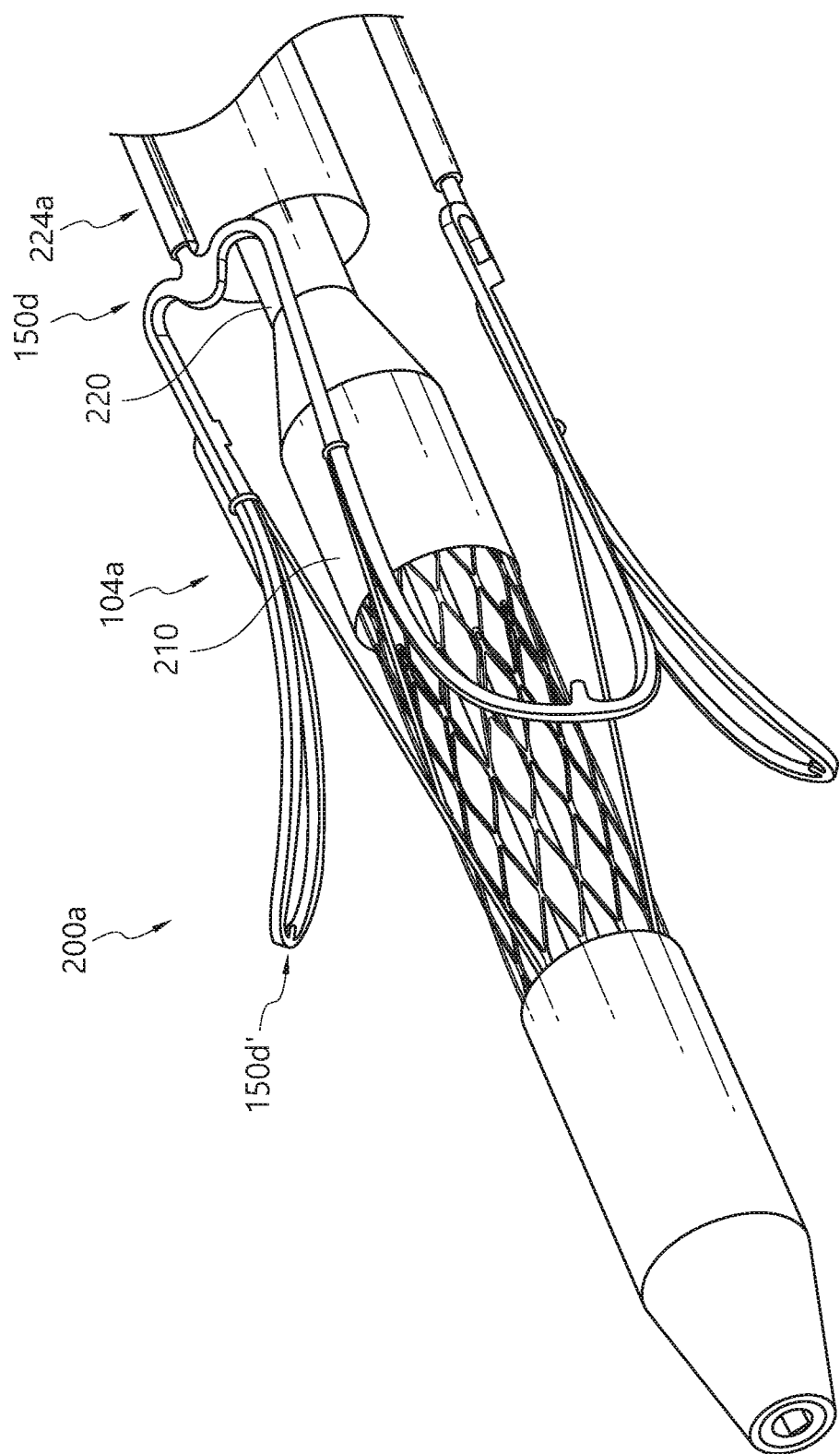
FIG. 4 is a perspective view the valve delivery device of FIG. 3 showing a grasper mechanism for engaging a valve anchor, according to some embodiments.

FIG. 4 illustrates aspects of the delivery device 200a, according to at least one embodiment. These figures do not illustrate all of the components of the delivery device that can be incorporated into an embodiment. However, the features illustrated in these figures can be incorporated into embodiments of the delivery device to facilitate engagement with the valve anchor and/or facilitate delivery and control of the valve anchor during implantation and release of the valve anchor at the target location.

For example, FIG. 4 illustrates an embodiment of a delivery device 200a that comprises a grasper mechanism. The grasper mechanism can be used to securely couple a portion of the valve anchor with the delivery device to permit the clinician to control movement, operation, and deployment of the valve anchor. The grasper mechanism can engage one or more portions or structures of the valve anchor using a variety of coupling mechanisms, which can use attachment means including mechanical engagement, dissolvable structures, chemically reactive degradable structures, electrolytically degradable structures, and the like.

In some embodiments, the grasper mechanism can be a tubular grasper mechanism. The delivery device 200a, shown in FIG. 4, can comprise a grasper 224a that can engage with and control the longitudinal position of the valve anchor 104a. The grasper 224a of the delivery device 200a can comprise an engagement wire that is movable within a lumen of a tubular enclosure. The valve anchor 104a can be configured to comprise a clasper tang extending from an engagement area 150d or 150d' of the valve anchor 104a. The engagement wire can comprise a distal end portion that includes pins, ridges, or protrusions that can be coupled to the engagement structure of the clasper tang at the engagement area of the valve anchor 104a. When engaged together, the engagement wire and the clasper tang can be proximally drawn into the lumen of the tubular enclosure, which secures the engagement wire and the clasper tang relative to each other in both radial and longitudinal directions. However, when the engagement wire and the clasper tang are moved outside of the lumen of the tubular enclosure, the engagement wire and the clasper tang can be disengaged as the valve anchor 104a and the clasper tang expand radially, thereby disengaging the clasper tang from the engagement wire. These and other features are discussed in U.S. Patent Application No. 62/781,537, noted above and incorporated herein by reference.

During use, after the valve anchor has been released from within the proximal sheath and after the valve anchor and the valve frame have been released from the delivery device, the delivery device can be configured to be compactly reassembled and withdrawn into the introducer sheath in order to minimize any damage to the blood vessel through which the delivery device was advanced.

For example, in at least one embodiment, as illustrated in FIG. 5A, the proximal enclosure 210 can comprise a proximal section 250 to facilitate realignment (e.g., radial realignment) of the distal end portion 208 of the proximal sheath component 204 with the proximal enclosure 210.

As illustrated in FIG. 5A, the proximal section 250 can be coupled to the core member 220. Further, the proximal section 250 can optionally be conical or tapered in a proximal direction and/or have circumferential nodes 252 and/or circumferential cavities 254 that can facilitate realignment of the proximal sheath component 204 relative to the proximal enclosure 210 along a longitudinal axis of the delivery device 200. The tapering of the proximal section 250 can allow the distal end portion 208 of the proximal sheath component 204 to smoothly advance distally over the proximal section 250, and the circumferential nodes 252 can contact an inner surface of the distal end portion 208 of the proximal sheath component 204 as the distal end portion 208 approaches the proximal abutment surface 214.

For example, as illustrated in FIG. 5A, the circumferential nodes 252 may gradually taper from the proximal abutment surface 214 in the proximal direction. With such a configuration, as the proximal sheath component 204 slides distally toward the proximal enclosure 210, the circumferential nodes 252 can advantageously guide the distal end portion 208 of the proximal sheath component 204 distally toward the proximal abutment surface 214 of the proximal enclosure 210 so that the outer surface of the proximal sheath component 204 is aligned with an outer surface of the proximal enclosure 210. Thus, the outer surfaces of the proximal enclosure 210 and the proximal sheath component 204 can provide a smooth outer profile for the delivery device 200 that can advantageously reduce the likelihood that the delivery device 200 catches or otherwise damages tissue within a body lumen as the delivery device 200 is moved therewithin.

Optionally, the proximal section 250 can comprise three circumferential nodes 252 and three circumferential cavities 254. The circumferential nodes 252 may extend proximally from the proximal abutment surface 214. The three circumferential cavities 254 can correspond to the number of U-shaped members of the valve anchor that are housed within the proximal sheath component 204 between the proximal sheath component 204 and the proximal section 250 of the proximal enclosure 210.

This advantageous feature of some embodiments can allow the distal enclosure 212 to be properly positioned along the delivery device 200 in order to ensure that distal enclosure 212 does not snag or become caught on any structure during retrieval of the delivery device 200.

As also shown in FIGS. 5A and 5B, the proximal and distal enclosures 210, 212 can collectively house the support frame 102. The first and second core members 220, 222 can be actuated to separate the proximal and distal enclosures 210, 212, thereby permitting the support frame 102 to self-expand when in position within the valve anchor 104.

For example, by pushing or pulling the first core member 220, the second core member 222, and/or the proximal sheath component 204 relative to each other along the longitudinal axis of the delivery device 200, a clinician can control longitudinal movement of each of these components to permit the release of the support frame 102 and the valve anchor 104 of the valve prosthesis 100.

Further, in some embodiments, to facilitate delivery of the delivery device 200 to the target location, as shown in FIGS. 5A and 5B, the second core member 222 can include a lumen 218 to permit the delivery device 200 to move along a guidewire, which can extend through the lumen 218 of the second core member 222.

FIGS. 5A and 5B further illustrate positions of the proximal and distal enclosures 210, 212 during the release of the support frame 102. After separating the proximal and distal enclosures 210, 212 from the position illustrated in FIG. 5A to the position illustrated in FIG. 5A, the first end portion 110 of the support frame 102 can begin to expand from the compressed configuration to an expanded configuration. In some embodiments, the support frame 102 can have one or more anchors 109 (see also FIG. 2) at its first end portion 110 that, when engaged with the native valve structure can supplement the outward expansive force (due to self-expansion of the support frame 102) and its resultant frictional engagement, to mitigate downstream migration of the support frame 102 relative to the native valve structure. Thus, by opening the first end portion 110 first (before the second end portion 112, and via relative movement of the proximal and distal enclosures 210, 212), the first end portion 110 can "flower" out to facilitate release of the support frame and/or to engage with the native anatomy, such as the valve structure itself, to secure a longitudinal position of the support frame 102 relative to the native valve structure. Thereafter, the second end portion 112 of the support frame 102 can be controlled and released to become disengaged and released from the proximal enclosure 210.

In some embodiments, the first end portion 110 and the second end portion 112 can open simultaneously, at the same or different rates. For example, in some embodiments, the first end portion 110 and the second end portion 112 can open simultaneously, but with the first end portion 110 opening at a faster rate than the second end portion 112.

Advantageously, the use of the proximal enclosure 210 and the distal enclosure 212 allows for greater control and enhanced operation of the support frame 102. For example, by controlling the position and rate of separation of the proximal enclosure 210 and the distal enclosure 212, the opening of the support frame 102 at both the first end portion 110 and the second end portion 112 can be controlled. Further, by controlling the movement of the distal enclosure 212, the timing and rate of opening of the first end portion 110 can be controlled relative to the timing and rate of opening of the second end portion 112 (which may be controlled by the movement of the proximal enclosure 210).

Additionally, and advantageously, by having separate proximal and distal enclosures 210, 212, the delivery device 200 may experience reduced frictional forces and minimize travel of the enclosures 210, 212 relative to the support frame 102.

In particular, in accordance with some embodiments, the distal carrier assembly 206 can comprise a plunger mechanism 260 that can facilitate expansion of the support frame 102. The plunger mechanism 260 can expand from a compressed state (shown in FIG. 5A) to an extended state (shown in FIG. 5A). The plunger mechanism 260 can be biased by a spring or other device in order to move automatically from the compressed state to the extended state. However, the plunger mechanism 260 can also be manually actuated by the clinician in some embodiments.

As illustrated, the plunger mechanism 260 can comprise a plunger head 262 and a biasing means 264. The plunger head 262 can comprise a conical or tapered proximal portion 286. The conical proximal portion 286 can be configured to not contact only the first end portion of the support frame 102 during delivery, but can also help center a distal end portion 290 of the tubular portion 282 of the proximal enclosure 210 relative to a longitudinal axis of the delivery device 200 and help align the distal end portion 290 with a proximal end portion 292 of the tubular portion 272 of the distal enclosure 212. The plunger head 262 can also comprise an outer circumferential surface 294 that can contact not only an inner surface 296 of the tubular portion 272, but can also contact an inner surface 298 of the tubular portion 282 when the tubular portion 282 is distally advanced over the conical proximal portion 286 of the plunger head 262.

Further, the plunger mechanism 260 can be housed within a distal lumen 270 of a tubular portion 272 of the distal enclosure 212. For example, the biasing means 264 may be a spring. The biasing means 264 can be interposed between an interior structure or wall 274 of the distal lumen 270 and a distal surface or structure 276 of the plunger head 262. The plunger head 262 can move proximally within the distal lumen 270 in order to continue to exert a proximally oriented force on the first end portion 110 of the support frame 102 until the support frame 102 exits the distal lumen 270. Thereafter, in accordance with some embodiments, the support frame 102 can self-expand until the second end portion 112 is pulled out of a proximal lumen 280 of a tubular portion 282 of the proximal enclosure 210 as the support frame 102 continues to expand. The expanded state of the support frame 102 is illustrated in FIGS. 1 and 2, discussed above.

The present disclosure also describes various aspects of a delivery device for, e.g., transfemoral delivery of a valve prosthesis. The delivery device can support a valve prosthesis, such as the prosthesis 100 discussed above. The delivery device can comprise a proximal sheath component, a distal carrier assembly, and a control unit, wherein the distal carrier assembly is distal to the proximal sheath component, and the proximal sheath component is distal to the control unit. In some embodiments, the distal carrier assembly can comprise a conical or tapered end portion. The proximal sheath component and the distal carrier assembly can at least partially enclose the support frame and the valve anchor of the valve prosthesis prior to and during delivery of the valve prosthesis. The configuration of the delivery device with respect to the proximal sheath component and the distal carrier assembly, the support frame, and the valve anchor can allow the valve anchor and the support frame to be loaded or positioned serially along the longitudinal axis in a compact condition, thus enabling the delivery device to achieve a minimal crossing profile to reduce any difficulty in advancing the delivery device to the target location within the patient. The distance from which the valve anchor may be serially displaced from the support frame is highly variable. This may allow the user to minimize the radius of the delivery device which must be advanced through, for example, arteries and veins. Further, the valve anchor can be expanded and positioned independent of the support frame prior to positioning and releasing the support frame, as described in greater detail below. Additionally, a link mechanism that interconnects the valve anchor to the support frame can advantageously facilitate reliable positioning of the support frame relative to the valve anchor.

Figure 6:
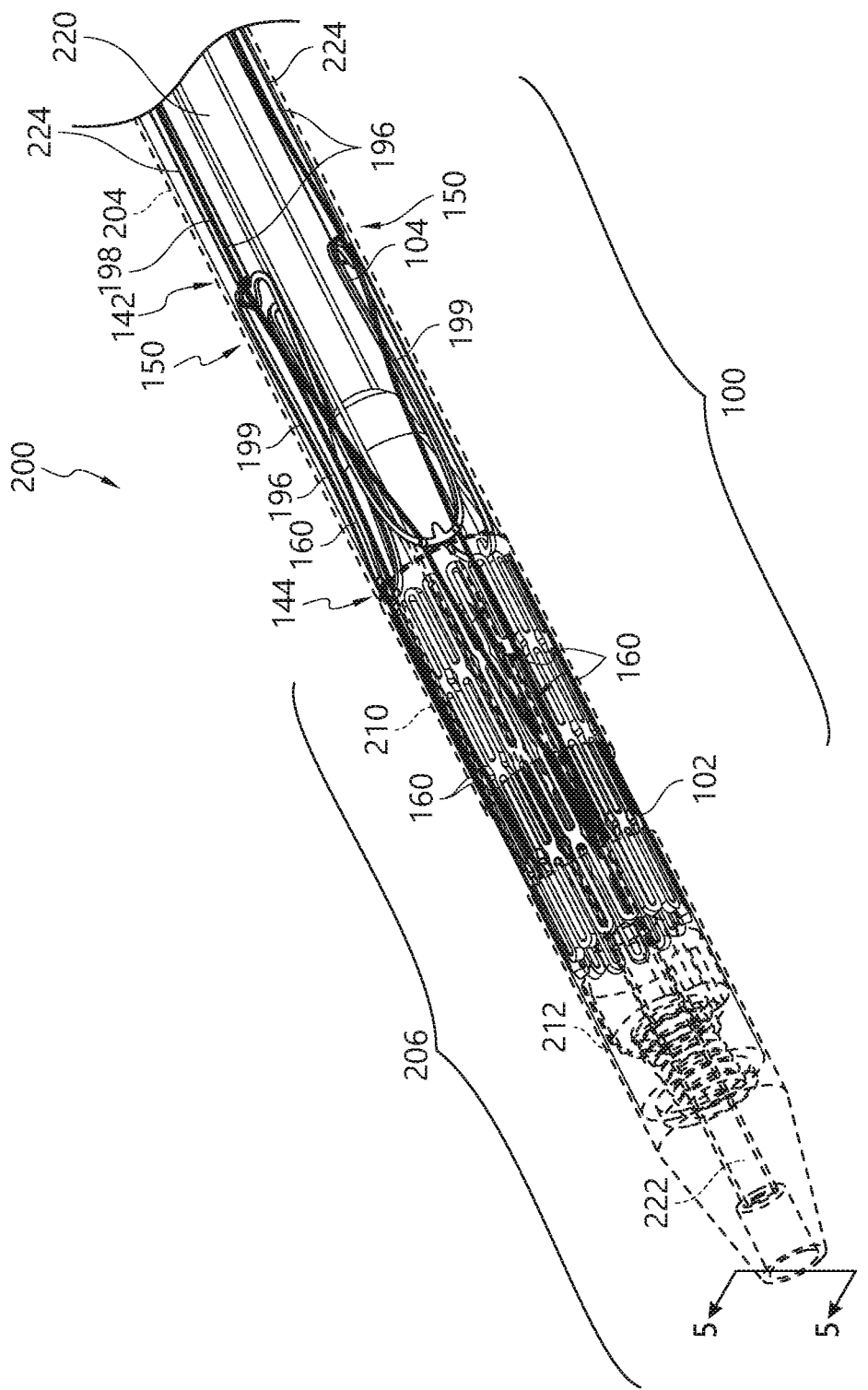
FIG. 6 shows an embodiments of a link mechanism for the valve prosthesis of FIG. 2, in which the valve prosthesis is loaded onto a valve delivery device, according to some embodiments.
Figure 7C:
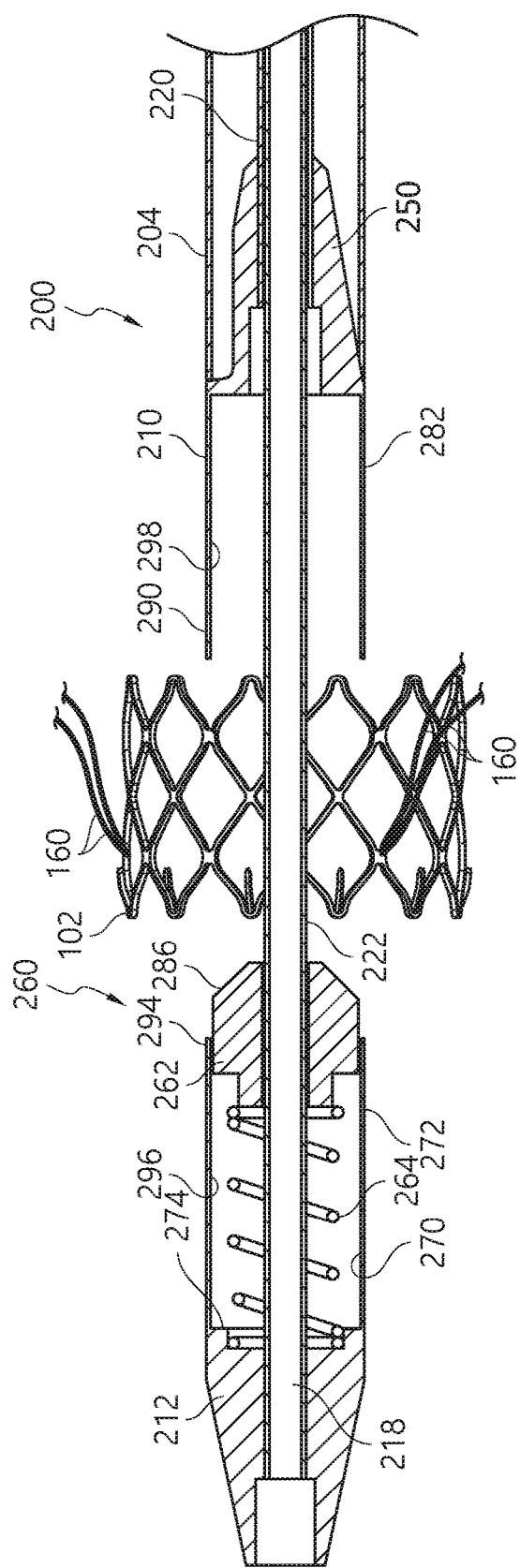
Figure 7D:
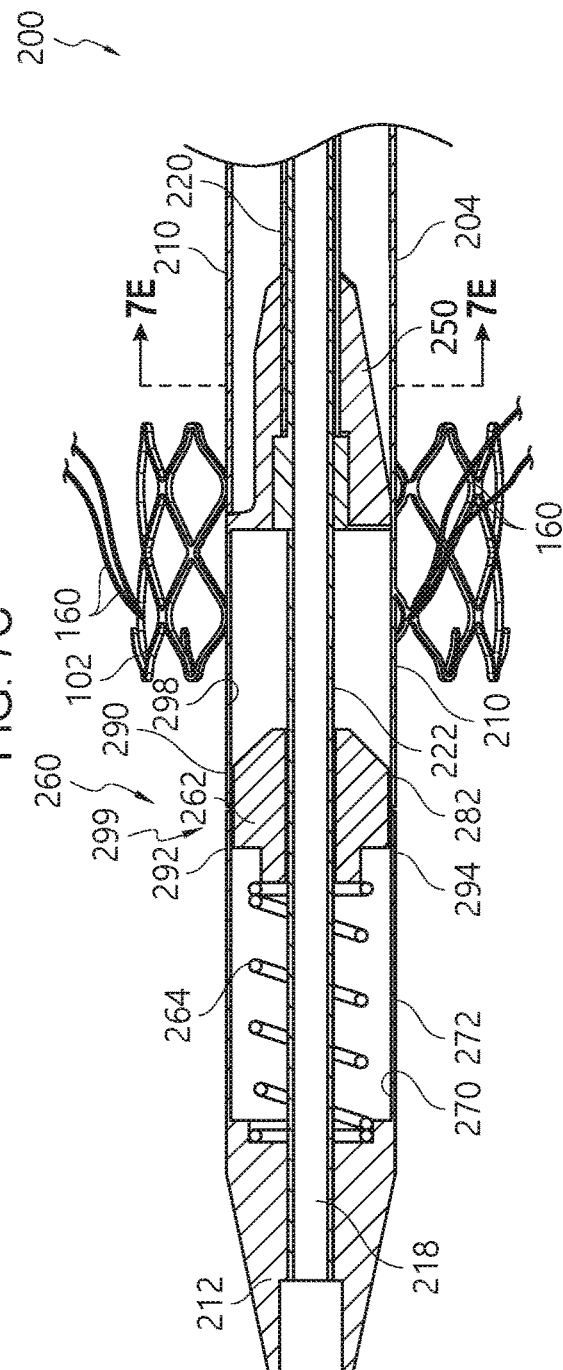

Referring now to FIGS. 6-7D, the prosthesis 100 is illustrated loaded onto a delivery device 200. Using the delivery device 200, the valve prosthesis 100 can be delivered and expanded component by component in order to achieve the expanded configuration illustrated in FIG. 2. During this component-by-component expansion process (illustrated in the delivery stages of FIGS. 11A-11F of U.S. Patent Application No. 62/781,537, filed on Dec. 18, 2018, noted above), the ability of the link mechanism 160 to move along the U-shaped members of the valve anchor 104 provides several distinct benefits. For example, one of these benefits is illustrated in FIG. 6, which is that during delivery of the valve prosthesis 100, it is advantageous to have the valve anchor 104 positioned serially from the support frame 102 in order to achieve a minimal outer profile for the delivery device. This serial positioning allows the delivery device 200 to have a minimized outer diameter, which can allow the delivery device 200 to be more easily advanced through blood vessels.

As shown in FIG. 6, the delivery device can carry the support frame, the valve anchor, and the link mechanism of the valve prosthesis. For example, FIG. 6 shows that the delivery device 200 can carry the support frame 102, the valve anchor 104, and the link mechanism 160 of the valve prosthesis 100. The delivery device 200 can comprise one or more elongate core members that extend along a longitudinal axis of the delivery device 200.

The delivery device 200 can also comprise a proximal sheath component 204 (shown in dashed lines in FIG. 6 to illustrate the underlying components and features of the prosthesis 100 and the delivery device 200) and a distal carrier assembly 206 (also shown in dashed lines in FIG. 6 to illustrate the underlying components and features of the prosthesis 100 and the delivery device 200). The proximal sheath component 204 can be coupled to and extend distal to a control unit (illustrated in FIGS. 13A-13H of U.S. Patent Application No. 62/781,537, filed on Dec. 18, 2018, noted above), through which the clinician can control movement of the various components of the delivery device 200.

The distal carrier assembly 206 can be a two-part component that is configured to house at least one of the valve anchor or the support frame. The distal carrier assembly 206 comprise a proximal enclosure 210 (shown in dashed lines) and a distal enclosure 212 (shown in dashed lines). The proximal enclosure 210 can be coupled to a first core member 220, and the distal enclosure 212 can be coupled to a second core member 222. In some embodiments, the distal enclosure 212 can be threadedly and/or adhesively coupled or bonded to the second core member 222. For example, the second core member 222 may include a hollow shaft. The first and second core members 220, 222 can allow a clinician to manipulate the relative positions of the proximal and distal enclosures 210, 212. Together, the proximal sheath component 204 and the distal carrier assembly 206 can collectively house the valve anchor 104 and the support frame 102, respectively, during delivery of the valve prosthesis 100 to a target location within the body (e.g., discussed herein as the aortic valve annulus) and be actuated by the clinician to position and release the valve prosthesis 100. Further, the distal enclosure 212 can comprise a conical or tapered anterior or distal portion to facilitate movement through the vasculature. In some embodiments, the distal carrier assembly 206 can be referred to as a two-part distal enclosure or a split nose cone assembly. Optionally, the distal enclosure 212 can comprise, be formed from, or include features that comprise a radiopaque material such as platinum.

FIG. 6 show the delivery device 200 prior to delivery of the prosthesis 100, in a loaded configuration. As shown, the first and second core members 220, 222 extend through the delivery device 200 and are coupled at their distal ends to proximal and distal enclosures 210, 212, respectively, of the distal carrier assembly 206. As illustrated in these figures, the second core member 222 can be disposed within a lumen of the first core member 220 and slidable therewithin. Accordingly, the proximal enclosure 210 of the distal carrier assembly 206, as well as the proximal sheath component 204, can be slidable relative to the second core member 222 and the distal enclosure 212.

As also shown, the proximal sheath component 204 can extend distally over the valve anchor 104 to enclose the valve anchor 104 within a lumen of the proximal sheath component 204 and maintain the valve anchor 104 in a compressed state. The lumen of the proximal sheath component 204 may also be referred to as a proximal sheath lumen. The proximal sheath component 204 can be retracted relative to the valve anchor 104 in order to permit the base portions of the U-shaped members of the valve anchor 104, thereafter to expand and later be maneuvered into position within the aortic sinuses.

As also illustrated in FIG. 6 (see also FIGS. 3A-3C of U.S. Patent Application No. 62/781,537, filed on Dec. 18, 2018, noted above), the delivery device 200 can comprise at least one grasper 224 that can engage with and control positioning of the valve anchor 104. The grasper 224 can comprise distal ends, pinchers, or hooks 226 at its distal end that can be coupled to the peak portions of the U-shaped members of the valve anchor 104. For example, the pinchers 226 of the grasper 224 can be coupled to the anchor retention component 170 at the engagement area of the valve anchor 104 to cause the grasper 224 to be engaged with the valve anchor 104. The number of graspers 224 preferably equals the number of engagement areas 150 or U-shaped members 140 of the valve anchor 104. Each of the graspers 224 can comprise a tubular enclosure 228 through which a pair of wires, which terminate in the pinchers or hooks 226, passes. The wires can be pulled proximally relative to the tubular enclosure 228 in which the wires are housed in order to tighten the pinchers 226 around the anchor retention component 170, thus engaging the valve anchor 104. In order to release the pinchers 226, the wires can be shifted distally relative to the tubular enclosure 228 thereby allowing the pinchers 226 to spring open radially and release the anchor retention component 170. The distal end of each of the graspers 224 can enclose or be coupled to a hook of the valve anchor 104.

The interconnection between the distal ends, pinchers, or hooks 226 of the graspers 224 and the valve anchor 104 can permit the valve anchor 104 of the support frame 102 to be held in a stationary and/or compressed position relative to or within the proximal sheath component 204. As discussed further below, for example, with regard to FIGS. 9A-9C, this engagement can maintain the engagement areas 150 in a common plane 152, oriented generally perpendicular relative to the longitudinal axis of the delivery device 200. Additionally, when the proximal sheath component 204 is proximally retracted relative to the distal ends of the graspers 224, the valve anchor 104 can begin to expand; however, the engagement between the graspers 224 and the engagement areas 150 can allow a clinician to push, pull, or rotate the valve anchor relative to the delivery device 200 before fully releasing the valve anchor 104 from engagement with the delivery device 200. For example, this can allow the clinician to rotate or push the base portions 144 of the valve anchor 104 into the nested position within the aortic sinuses, as discussed above. Thereafter, once in the nested position, the engagement areas 150 of the valve anchor 104 can be released from the pinchers 226 of the graspers 224, and the valve anchor 104 can fully expand and be released into apposition with the native valve annulus.

Accordingly, in at least one embodiment, a clinician can manipulate the valve anchor by engaging or coupling an engagement portion or protrusion of a grasper with a clasper tang of a valve anchor. The engagement portion and the clasper tang can be restricted from relative radial movement (to thereby remain longitudinally engaged and secured relative to each other) by enclosing the engagement portion and the clasper tang within a tubular enclosure. In order to disengage the engagement portion and the clasper tang, the clinician can relatively advance the engagement portion distally beyond an end of the tubular enclosure. Once in this position, the clasper tang can tend to be pulled radially outwardly as the valve anchor expands radially, thereby disengaging the clasper tang from the engagement portion. Thereafter, the engagement portion can be retracted or withdrawn into the tubular enclosure. In some embodiments, the engagement portion engages a window or protrusion of the clasper tang. In some embodiments, the engagement portion is a pin or slot. In some embodiments, each grasper can include a plurality of engagement portions or protrusions.

During use, after the valve anchor has been released from within the proximal sheath and after the valve anchor and the valve frame have been released from the delivery device, the delivery device can be configured to be compactly reassembled and withdrawn into the introducer sheath in order to minimize any damage to the blood vessel through which the delivery device was advanced.

For example, in at least one embodiment, as illustrated in FIG. 7A, the proximal enclosure 210 can comprise a proximal section 250 to facilitate realignment (e.g., radial realignment) of the distal end portion 208 of the proximal sheath component 204 with the proximal enclosure 210.

As illustrated in FIG. 7A, the proximal section 250 can be coupled to the core member 220. Further, the proximal section 250 can optionally be conical or tapered in a proximal direction and/or have circumferential nodes 252 and/or circumferential cavities 254 that can facilitate realignment of the proximal sheath component 204 relative to the proximal enclosure 210 along a longitudinal axis of the delivery device 200. The tapering of the proximal section 250 can allow the distal end portion 208 of the proximal sheath component 204 to smoothly advance distally over the proximal section 250, and the circumferential nodes 252 can contact an inner surface of the distal end portion 208 of the proximal sheath component 204 as the distal end portion 208 approaches the proximal abutment surface 214.

For example, as illustrated in FIG. 7A, the circumferential nodes 252 may gradually taper from the proximal abutment surface 214 in the proximal direction. With such a configuration, as the proximal sheath component 204 slides distally toward the proximal enclosure 210, the circumferential nodes 252 can advantageously guide the distal end portion 208 of the proximal sheath component 204 distally toward the proximal abutment surface 214 of the proximal enclosure 210 so that the outer surface of the proximal sheath component 204 is aligned with an outer surface of the proximal enclosure 210. Thus, the outer surfaces of the proximal enclosure 210 and the proximal sheath component 204 can provide a smooth outer profile for the delivery device 200 that can advantageously reduce the likelihood that the delivery device 200 catches or otherwise damages tissue within a body lumen as the delivery device 200 is moved therewithin.

Optionally, the proximal section 250 can comprise three circumferential nodes 252 and three circumferential cavities 254. The circumferential nodes 252 may extend proximally from the proximal abutment surface 214. The three circumferential cavities 254 can correspond to the number of U-shaped members of the valve anchor that are housed within the proximal sheath component 204 between the proximal sheath component 204 and the proximal section 250 of the proximal enclosure 210.

This advantageous feature of some embodiments can allow the distal enclosure 212 to be properly positioned along the delivery device 200 in order to ensure that distal enclosure 212 does not snag or become caught on any structure during retrieval of the delivery device 200.

As also shown in FIGS. 6-7B, the proximal and distal enclosures 210, 212 can collectively house the support frame 102. The first and second core members 220, 222 can be actuated to separate the proximal and distal enclosures 210, 212, thereby permitting the support frame 102 to self-expand when in position within the valve anchor 104.

For example, by pushing or pulling the first core member 220, the second core member 222, and/or the proximal sheath component 204 relative to each other along the longitudinal axis of the delivery device 200, a clinician can control longitudinal movement of each of these components to permit the release of the support frame 102 and the valve anchor 104 of the valve prosthesis 100.

Further, in some embodiments, to facilitate delivery of the delivery device 200 to the target location, as shown in FIGS. 7A-7D, the second core member 222 can include a lumen 218 to permit the delivery device 200 to move along a guidewire, which can extend through the lumen 218 of the second core member 222.

FIGS. 7A-7D further illustrate positions of the proximal and distal enclosures 210, 212 during the release of the support frame 102. After separating the proximal and distal enclosures 210, 212 from the position illustrated in FIG. 7A to the position illustrated in FIG. 7B, the first end portion 110 of the support frame 102 can begin to expand from the compressed configuration to an expanded configuration. In some embodiments, the support frame 102 can have one or more anchors 109 (see also FIG. 2) at its first end portion 110 that, when engaged with the native valve structure can supplement the outward expansive force (due to self-expansion of the support frame 102) and its resultant frictional engagement, to mitigate downstream migration of the support frame 102 relative to the native valve structure. Thus, by opening the first end portion 110 first (before the second end portion 112, and via relative movement of the proximal and distal enclosures 210, 212), the first end portion 110 can "flower" out to facilitate release of the support frame and/or to engage with the native anatomy, such as the valve structure itself, to secure a longitudinal position of the support frame 102 relative to the native valve structure. Thereafter, the second end portion 112 of the support frame 102 can be controlled and released to become disengaged and released from the proximal enclosure 210.

In some embodiments, the first end portion 110 and the second end portion 112 can open simultaneously, at the same or different rates. For example, in some embodiments, the first end portion 110 and the second end portion 112 can open simultaneously, but with the first end portion 110 opening at a faster rate than the second end portion 112.

Advantageously, the use of the proximal enclosure 210 and the distal enclosure 212 allows for greater control and enhanced operation of the support frame 102. For example, by controlling the position and rate of separation of the proximal enclosure 210 and the distal enclosure 212, the opening of the support frame 102 at both the first end portion 110 and the second end portion 112 can be controlled. Further, by controlling the movement of the distal enclosure 212, the timing and rate of opening of the first end portion 110 can be controlled relative to the timing and rate of opening of the second end portion 112 (which may be controlled by the movement of the proximal enclosure 210).

Additionally and advantageously, by having separate proximal and distal enclosures 210, 212, the delivery device 200 may experience reduced frictional forces and minimize travel of the enclosures 210, 212 relative to the support frame 102.

In particular, in accordance with some embodiments, the distal carrier assembly 206 can comprise a plunger mechanism 260 that can facilitate expansion of the support frame 102. The plunger mechanism 260 can expand from a compressed state (shown in FIG. 7A) to an extended state (shown in FIG. 7B). The plunger mechanism 260 can be biased by a spring or other device in order to move automatically from the compressed state to the extended state. However, the plunger mechanism 260 can also be manually actuated by the clinician in some embodiments.

As illustrated, the plunger mechanism 260 can comprise a plunger head 262 and a biasing means 264. Further, the plunger mechanism 260 can be housed within a distal lumen 270 of a tubular portion 272 of the distal enclosure 212. For example, the biasing means 264 may be a spring. The biasing means 264 can be interposed between an interior structure or wall 274 of the distal lumen 270 and a distal surface or structure 276 of the plunger head 262. The plunger head 262 can move proximally within the distal lumen 270 in order to continue to exert a proximally oriented force on the first end portion 110 of the support frame 102 until the support frame 102 exits the distal lumen 270. Thereafter, in accordance with some embodiments, the support frame 102 can self-expand until the second end portion 112 is pulled out of a proximal lumen 280 of a tubular portion 282 of the proximal enclosure 210 as the support frame 102 continues to expand. The expanded state of the support frame 102 is illustrated in FIGS. 7C and 7D.

Some embodiments can also provide self-aligning features to allow the components of the delivery assembly to be moved from a releasing state (where the components of the valve prosthesis are released from engagement with the delivery assembly) to a nested or stowed state in which the delivery assembly has an aligned outer surfaces or outer surfaces that abut at a seam outer profile that can tend to reduce the likelihood of snagging on the vasculature as the delivery assembly is retrieved from the patient's vasculature. For example, optionally, after the support frame 102 has been expanded and released from the distal carrier assembly 206, the plunger head 262 can advantageously facilitate repositioning and realignment of the proximal and distal enclosures 210, 212 of the distal carrier assembly 206 in preparation for removal of the delivery device 200 from the patient.

For example, the plunger head 262 can comprise a conical or tapered proximal portion 286. The conical proximal portion 286 can be configured to not contact only the first end portion of the support frame 102 during delivery, but can also help center a distal end portion 290 of the tubular portion 282 of the proximal enclosure 210 relative to a longitudinal axis of the delivery device 200 and help align the distal end portion 290 with a proximal end portion 292 of the tubular portion 272 of the distal enclosure 212.

Further, in some embodiments, the plunger head 262 can extend proximally at least partially out of or from the tubular portion 272 of the distal enclosure 212. For example, the plunger head 262 can comprise an outer circumferential surface 294 that can contact not only an inner surface 296 of the tubular portion 272, but can also contact an inner surface 298 of the tubular portion 282 when the tubular portion 282 is distally advanced over the conical proximal portion 286 of the plunger head 262. As such, distal end portion 290 of the proximal enclosure 210 can positioned in an abutting contact position 299 with the proximal end portion 292 of the distal enclosure 212, as shown in FIG. 7D. Thus, the plunger mechanism 260 can facilitate not only be expansion of the support frame 102, but can also facilitate the self-alignment and repositioning of the proximal and distal enclosures 210, 212 in order to ensure that neither the proximal enclosure 210 nor the distal enclosure 212 snags or becomes caught on any structure during retrieval of the delivery device 200.

In accordance with at least one embodiment disclosed herein, the delivery device can optionally comprise a plunger mechanism having features that can expand radially beyond the outer diameter of the tubular portion 272 of the distal enclosure 212. Further, the plunger mechanism can also be configured in a manner to engage a proximal end of the tubular portion 272 of the distal enclosure 212. Thus, instead of the plunger mechanism 260 illustrated in the embodiment shown in FIGS. 7A-7D, the delivery device can optionally comprise a nose cone protector that can facilitate expansion of the support frame and advantageously provide a contact surface or ramp that tapers from a first diameter to a second, larger diameter in a distal direction to avoid or reduce any catching or engagement of the delivery device 200 when being proximally withdrawn into the delivery catheter. Further, the nose cone protector can increase the column strength of the nose cone or the distal carrier assembly 206. In this manner, the nose cone protector can help avoid breakage or dislocation of the nose cone or distal carrier assembly 206 when the clinician is exerting a proximal retraction force on the delivery assembly 200 to retract the delivery device 200 into the delivery catheter.

For example, FIGS. 8A-8F illustrate a nose cone protector 260a that can facilitate expansion of the support frame 102, similar to the plunger mechanism 260 illustrated in FIGS. 7A-7D. The nose cone protector 260a can move longitudinally from a compressed state (shown in FIG. 8B) to an extended state (shown in FIG. 8C). The nose cone protector 260a can be biased by a spring or other device in order to move automatically from the compressed state to the extended state. However, the nose cone protector 260a can also be manually actuated by the clinician, in some embodiments.

Figure 8A:
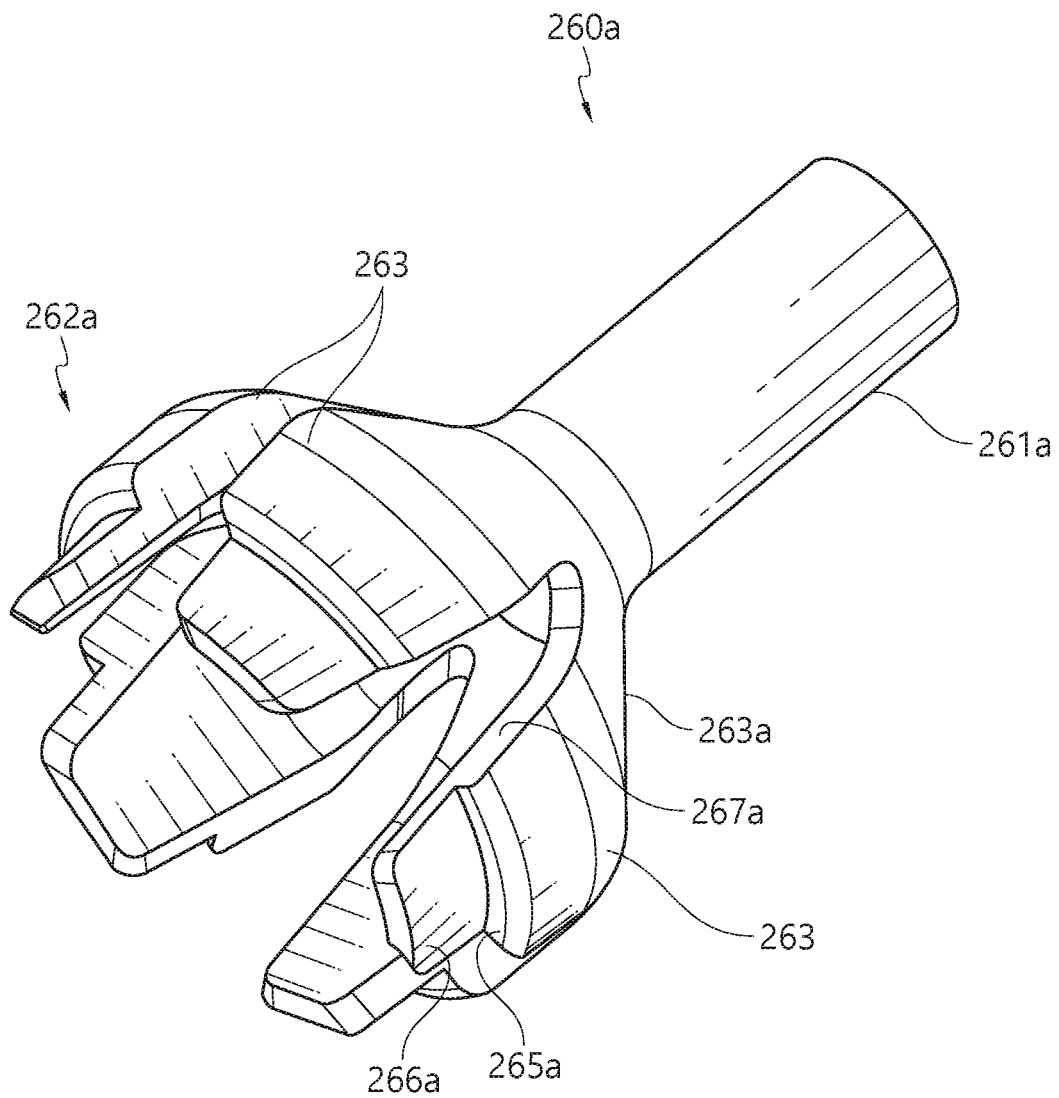
FIG. 8A is a perspective view of a nose cone protector, according to some embodiments.

As shown in FIG. 8A, the nose cone protector 260a can comprise a plunger head 262a having petals 263 that each extend radially from the nose cone protector 260a and comprise ramped surfaces 263a. The ramped surfaces 263a can be configured to engage a distal end of the support frame 102 and urge the support frame 102 out of the distal enclosure 212, similar to the plunger mechanism 260 discussed above, which can facilitate expansion of the support frame 102. In some embodiments, the nose cone protector 260a can comprise polyether ether ketone (PEEK) or other thermoplastics.

In at least one embodiment, the petals 263 can be configured to deflect radially inwardly while the nose cone protector 260a is positioned within the lumen of the distal enclosure 212, but to expand radially outwardly when at least a portion of the petals 263 exits the distal enclosure 212, as discussed below. Thus, the petals 263 can be resiliently biased toward a radially expanded position.

Additionally, the nose cone protector 260a can comprise a central lumen 261a through which the core member 220 of the delivery device 200 can extend. In this regard, the nose cone protector 260a can be permitted to slide along the core member of the delivery device.

Further, the nose cone protector 260a can be used with the distal carrier assembly 206 to ensure that neither the proximal enclosure 210 nor the distal enclosure 212 snags or becomes caught on the delivery catheter or any anatomical structure during retrieval of the delivery device 200. In at least one embodiment, the ramped surfaces 263a of the nose cone protector 260a can also facilitate self-alignment and repositioning of the proximal and distal enclosures 210, 212 similar to that provided by the plunger mechanism 260.

In use, because the nose cone protector 260a provides a smooth, ramped surface that the delivery device 200 can contact against any protuberances of the anatomical structure or delivery catheter, the nose cone protector 260a can thereby advantageously minimize the pulling or retraction force required by the clinician during retraction of the delivery device 200 into the delivery catheter. Of course, another beneficial effect of the nose cone protector 260a is to prevent or reduce any trauma to the blood vessel.

As illustrated, the nose cone protector 260a can be biased to spring radially outward to engage against the proximal end of the distal enclosure 212 in its extended state. In the extended state, the petals 263 can spread apart at separations 267a. Further, the petals 263 can each comprise an engagement tooth 266a that has an outer surface that is radially offset from an outer surface of its respective petal 263, thereby permitting the petal 263 to expand radially beyond an inner diameter of the distal enclosure 212. The teeth 266a can have a contact surface that is radially offset from an outer surface of the petals 263. Further, when the teeth 266 engage the proximal end of the distal enclosure 212, the outer surfaces of the petals 263 can extend radially beyond the outer surface of the distal enclosure 212.

In some embodiments, a distal engagement surface 265a of each petal 263 can abut the proximal end of the distal enclosure 212. As illustrated, the ramped surface 263a of the nose cone protector 260a can align and facilitate repositioning of the proximal and distal enclosures 210, 212 relative to each other in anticipation of proximally withdrawing the delivery device 200 into the delivery catheter 530. Additionally, the ramped surface 263a of the nose cone protector 260a can provide an angled surface that will not tend to snag or engage a distal end 531 of the delivery catheter 530 (see FIG. 8F).

As illustrated in FIG. 8B, the nose cone protector 260a can be housed within a distal lumen 270 of a tubular portion 272 of the distal enclosure 212. The nose cone protector 260a can be coupled to and urged proximally out of the distal enclosure 212 via a biasing means 264. As described with respect to the plunger mechanism 260, the biasing means 264 may be a spring. The petals 263 can be radially compressed to be housed within the distal lumen 270. The biasing means 264 can be interposed between an interior structure or wall 274 of the distal lumen 270 and a distal surface or structure 276 of the plunger head 262a. The plunger head 262a can move proximally within the distal lumen 270 in order to continue to exert a proximally oriented force on the first end portion 110 of the support frame 102 until the support frame 102 exits the distal lumen 270. Thereafter, in accordance with some embodiments, the support frame 102 can self-expand until the second end portion 112 is pulled out of a proximal lumen 280 of a tubular portion 282 of the proximal enclosure 210 as the support frame 102 continues to expand. The expanded state of the support frame 102 is illustrated in FIGS. 8C-8F.

Figure 8D:
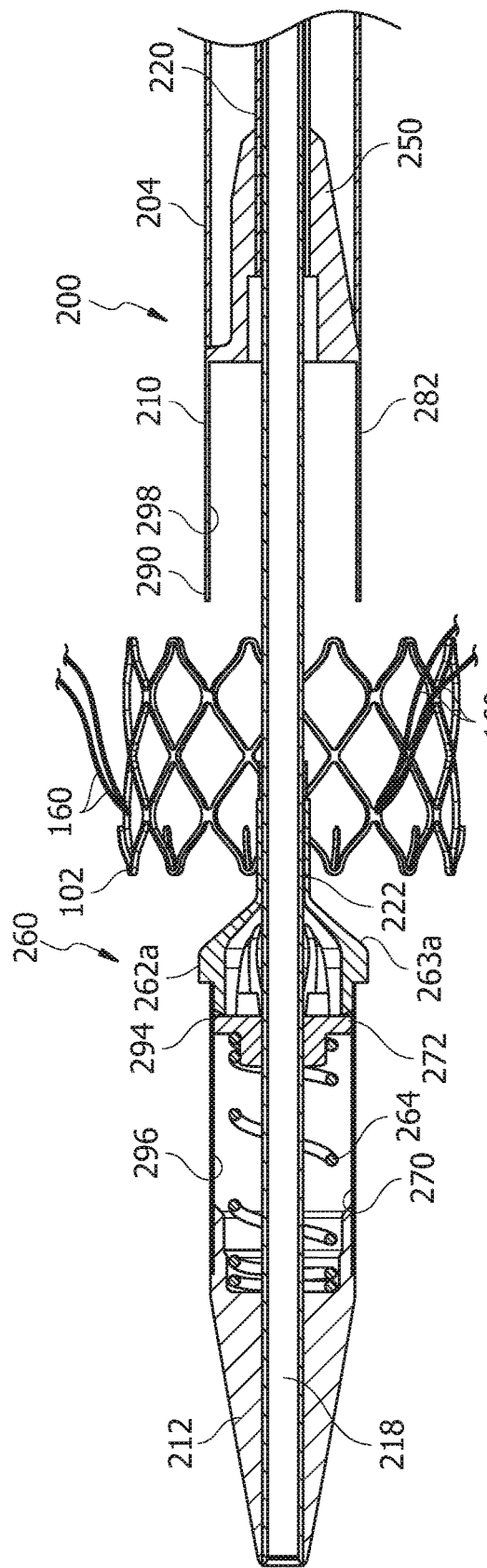

As illustrated in FIGS. 8C and 8D, as the nose cone protector 260a advances (FIG. 8C shows the nose cone protector 260a in a semi-expanded state) and the distal engagement surface 265a extends past the proximal end of the distal lumen 270 (FIG. 8D shows the nose cone protector 260a in a fully expanded state), the petals 263 can radially expand to engage against the distal lumen 270. Optionally, the proximal end of the nose cone protector 260a can be axially retained by collar engaged against the central lumen 261a to maintain the distal engagement surface 265a in axial abutment with the proximal end of the distal enclosure 212.

Figure 8E:
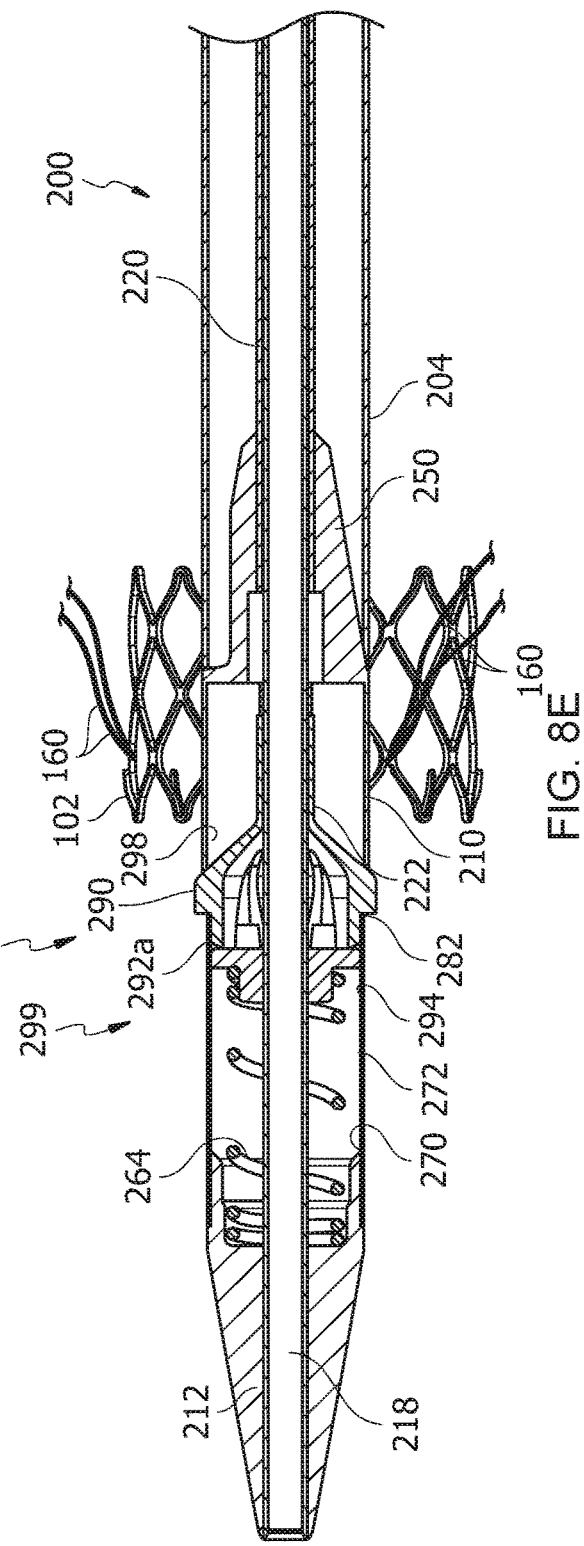

In addition to contacting the first end portion of the support frame 102 during delivery, as shown in FIG. 8E, the ramped surface 263a can also help center a distal end portion 290 of the tubular portion 282 of the proximal enclosure 210 relative to a longitudinal axis of the delivery device 200 and help align the distal end portion 290 with a proximal end portion 292 of the tubular portion 272 of the distal enclosure 212.

Figure 8F:
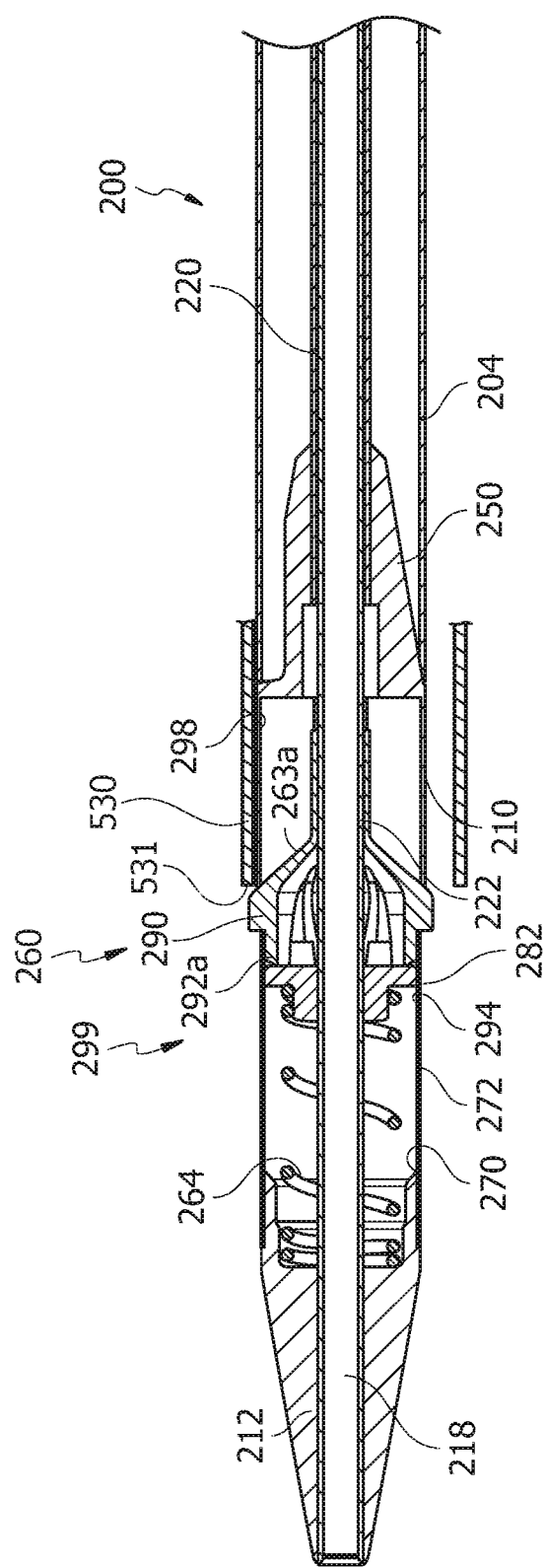

Further, as shown in FIG. 8F, in some embodiments, the ramped surface 263a allows the proximal sheath component 204 to be concentrically aligned with the distal enclosure 212, minimizing the retraction force required to retract the proximal and distal enclosure 210, 212 into the proximal sheath component. In some embodiments, the ramped surface 263a can have a ramp angle of approximately 45 degrees, or may range from between about 10 degrees to about 80 degrees, from between about 20 degrees to about 70 degrees, from between about 30 degrees to about 60 degrees, or from between about 40 degrees to about 50 degrees.

Figure 9A:
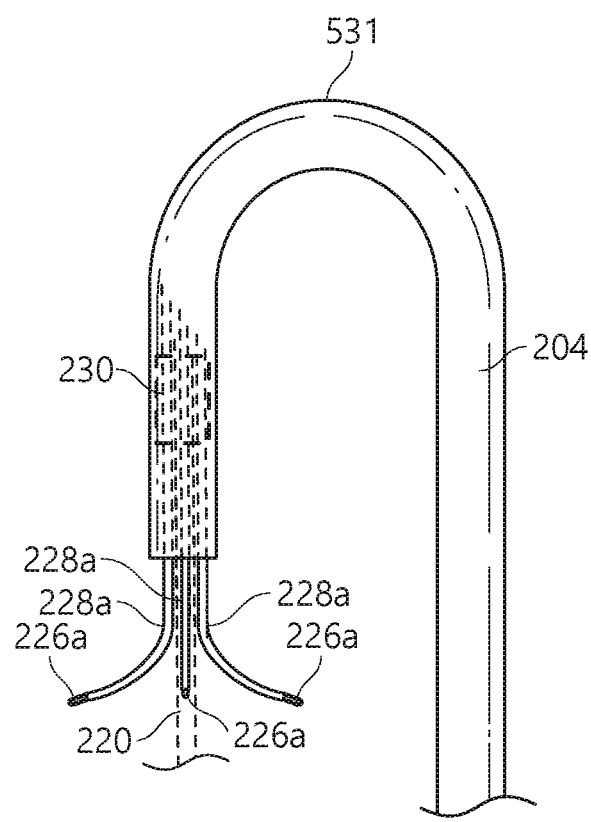
FIGS. 9A and 9B are views of a valve delivery device having a grasper mechanism with a grasper alignment hub, according to some embodiments.
Figure 9B:
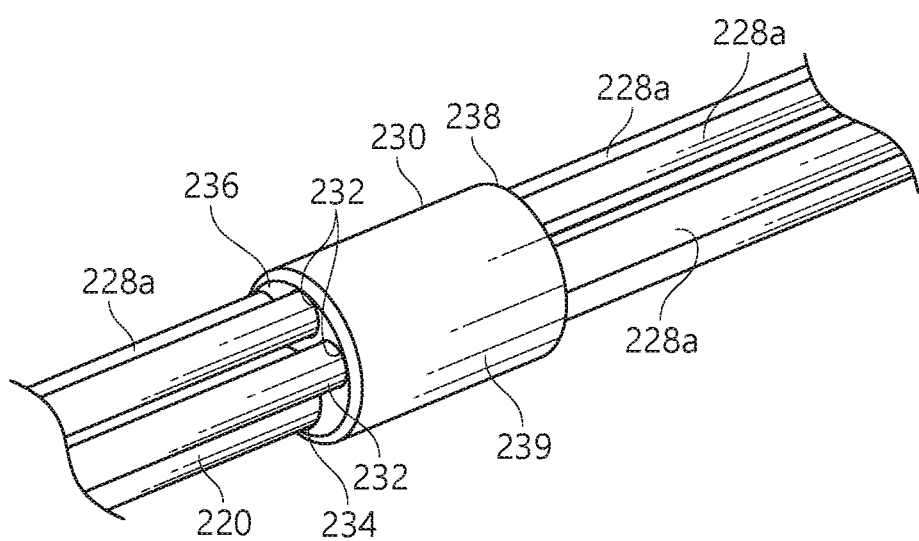
Figure 9C:
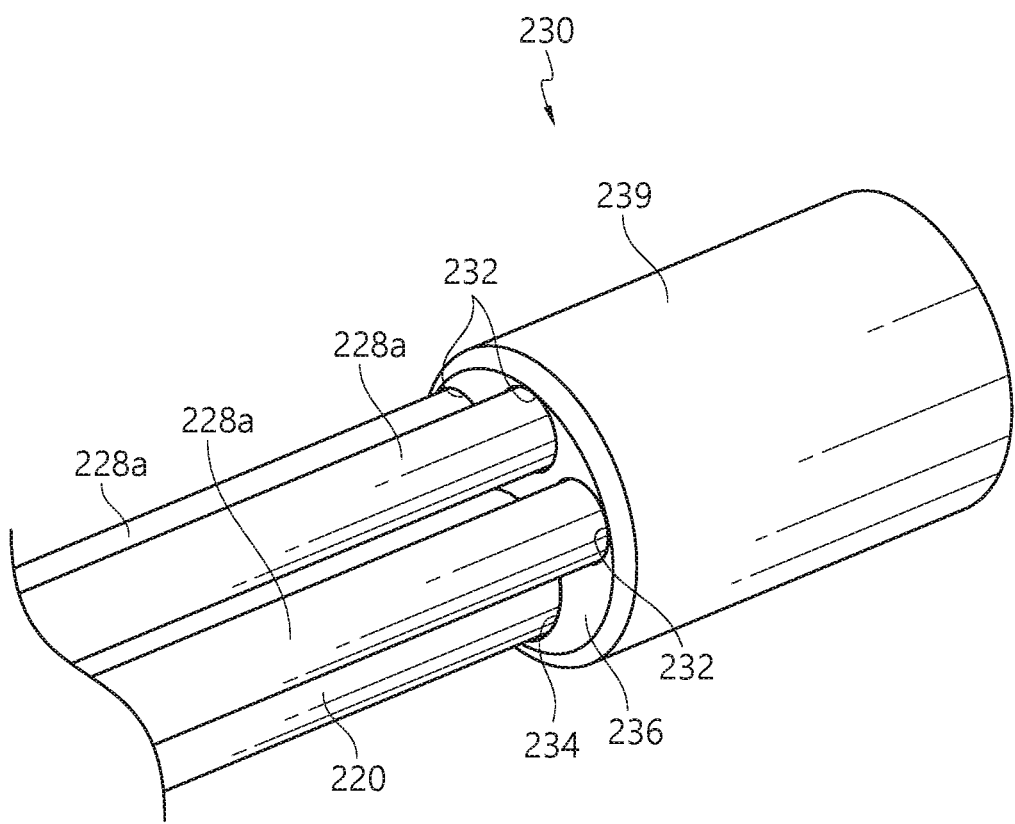
FIG. 9C is a view of the grasper alignment hub assembly of FIG. 9B, according to some embodiments.

FIGS. 9A-9C illustrate optional aspects of a delivery device, according to at least one embodiment. These figures do not illustrate all of the components of the delivery device that can be incorporated into an embodiment. However, the features illustrated in these figures can be incorporated into embodiments of the delivery device to facilitate engagement with the valve anchor and/or facilitate delivery and control of the valve anchor during implantation and release of the valve anchor at the target location.

In accordance with at least one embodiment disclosed herein is the realization that when the delivery device is moved through a blood vessel, the delivery device may be bent or curved as it passes through a tortuosity of the blood vessel. When this happens, the graspers may tend to move radially within the proximal sheath component, which may cause the distal or engagement ends of the graspers to become longitudinally displaced or misaligned relative to each other. This may cause bending or misalignment of the valve anchor during delivery, which may make placement more challenging.

More specifically, in at least one embodiment, the grasper mechanisms may extend from a handle actuator (see e.g., FIGS. 13A-13H of U.S. Patent Application No. 62/781,537, filed on Dec. 18, 2018, noted above) from a common plane (that may be oriented generally perpendicular relative to a longitudinal axis of the delivery device) and have approximately equal longitudinal lengths. Additionally, each of the grasper mechanisms may originate from a given radial or circumferential position, sector, or quadrant within the proximal sheath component. If the delivery device extends along a straight path, the distal or engagement ends of the graspers will also be aligned in a common plane that is oriented generally perpendicular relative to the longitudinal axis of the delivery device thereby engaging with the areas of the valve anchor, as shown in FIG. 5 of U.S. Patent Application No. 62/781,537, filed on Dec. 18, 2018, noted above.

However, in use, if the proximal sheath component bends (as shown in FIG. 9A), e.g., due to a tortuosity of the blood vessel, each of the grasper mechanisms may be moved out of its original circumferential or radial position, sector, or quadrant within the proximal sheath component. This occurs because each individual grasper mechanism will tend to extend in a straight, linear path within the proximal sheath component and only bend if the grasper mechanism hits the inner wall of the proximal sheath component. As a result, the grasper mechanisms may converge against an outer wall of a bend in the proximal sheath component, which can change the relative positioning of the distal or engagement ends of the graspers. Accordingly, instead of being aligned or positioned within a common plane that is oriented generally perpendicular relative to a longitudinal axis of the proximal sheath component, the distal or engagement ends of the graspers may be positioned out of plane or simply out of the common plane that extends perpendicular relative to the longitudinal axis of the proximal sheath component. Such a misalignment can create stress, misalignment, unintentional disengagement, or bending of the valve anchor, whose engagement areas are most preferably maintained within a common plane (that is oriented generally perpendicular relative to a longitudinal axis of the proximal sheath component) during delivery.

Therefore, at least one embodiment can be configured to include an alignment hub that can maintain or fix a longitudinal position of at least a portion of the grasper mechanisms along distal portion of the grasper mechanisms. In this manner, although intermediate portions of the grasper mechanisms may be radially misaligned or displaced from their original radial or circumferential position, sector, or quadrant within the proximal sheath component, the alignment hub can advantageously serve to reset or realign the positions of the grasper mechanisms so that the longitudinal positions of the can be located within substantially the same or common plane positioned perpendicularly relative to a longitudinal axis of the proximal sheath component.

For example, FIGS. 9A-9C illustrate a distal hub or grasper alignment hub 230 that may optionally be used in at least one embodiment of the delivery device. As illustrated, the grasper alignment hub 230 can be utilized to fix or maintain the distal ends of the graspers 226a in a desirable common plane to allow for desired and/or predictable engagement and disengagement of the graspers 226a with the valve anchor 104. In particular, the grasper alignment hub 230 can allow the distal ends of the graspers 226a to be maintained in a common plane despite bending of a proximal sheath component 204 530 as is manipulated through or past tortuosities of a blood vessel, e.g., at a bend.

As illustrated in FIGS. 9A and 9B, the grasper alignment hub 230 can be bonded or secured relative or directly to the tubular enclosures 228a of the graspers 226a near the distal section of the delivery device. In some embodiments, the grasper alignment hub 230 can be secured to the tubular enclosures 228a at least approximately 1 inch, 2 inches, 3 inches, 3.5 inches, or 4 inches from the distal end of the delivery device.

Referring to FIG. 9B, the graspers 226a and the corresponding tubular enclosures 228a extend through the grasper alignment hub 230, between a first or proximal end 236 to a second or distal end 238 through tubular enclosure passages 232 formed through the grasper alignment hub 230. The tubular enclosures 228a can be bonded or mechanically coupled to the tubular enclosure passages 232 so as to engage or secure the tubular enclosures 228a relative to the grasper alignment hub 230. Even though the tubular enclosures 228a may be constrained from longitudinal movement along the distal section of the delivery device relative to the grasper alignment hub 230, in some embodiments, the graspers 226a may still be permitted to move within the tubular enclosures 228a to facilitate engagement and/or disengagement with the valve anchor. However, because the tubular enclosures 228a are constrained from sliding movement, the distal ends of the graspers 226a may also be restricted from being longitudinally displaced relative to each other when the proximal sheath component 204 moves through or is moved into a curve or tortuosity, tend to be longitudinally displaced relative to each other less than in an embodiment As illustrated, the core member 220 can pass through the first or proximal end 236 to the second or distal end 238 through a core member passage 234 formed through the grasper alignment hub 230. The core member 220 can be movable through the core member passage 234. For example, in some embodiments, the grasper alignment hub 230 can move relative to the core member 220 while the tubular enclosures 228a are secured to the grasper alignment hub 230.

Referring to FIG. 9C, the outer surface 239 of the grasper alignment hub 230 can have a generally cylindrical shape. In some embodiments, the cylindrical shape of the outer surface 239 can allow the grasper alignment hub 230 to move freely within the catheter 530. As illustrated, the tubular enclosure passages 232 and the core member passage 234 can be arranged to maintain a desired alignment between the tubular enclosures 228a and the core member 220 as the catheter 530 is manipulated during introduction and delivery. Further, in at least one embodiment, the cross-sectional arrangement of the tubular enclosure passages 232 and the core member 220 at the grasper alignment hub 230 can be substantially similar to their cross-sectional arrangement at the handle actuator.

Additionally, in accordance with at least one embodiment, the arrangement of the tubular enclosure passages 232 and the core member passage 234 and the grasper alignment hub 230 can further reduce or avoid twisting or misalignment of the tubular enclosures 228a and the core member 220 relative to the longitudinal axis of the lumen of the catheter 530.

As illustrated, in at least one embodiment, the tubular enclosure passages 232 may be disposed adjacent to each other, offset from a central axis of the grasper alignment hub 230, along an arc bordering a periphery of the grasper alignment hub 230. The core member passage 234 can have a cross-sectional diameter larger than the respective cross-sectional diameters of the tubular enclosure passages 232. The core member passage 234 can be offset from the central axis of the grasper alignment hub 230 and be spaced apart from the tubular enclosure passages 232. Such a configuration can allow the grasper alignment hub 232 have a minimal cross-sectional diameter while permitting each of the tubular enclosure passages 232 and the core member passage 234 to be circumscribed therewithin.

However, in at least one embodiment, the tubular enclosure passages 232 may be disposed circumferentially around the core member passage 234. Optionally, the tubular enclosure passages 232 may be equidistantly disposed.

Figure 7E:
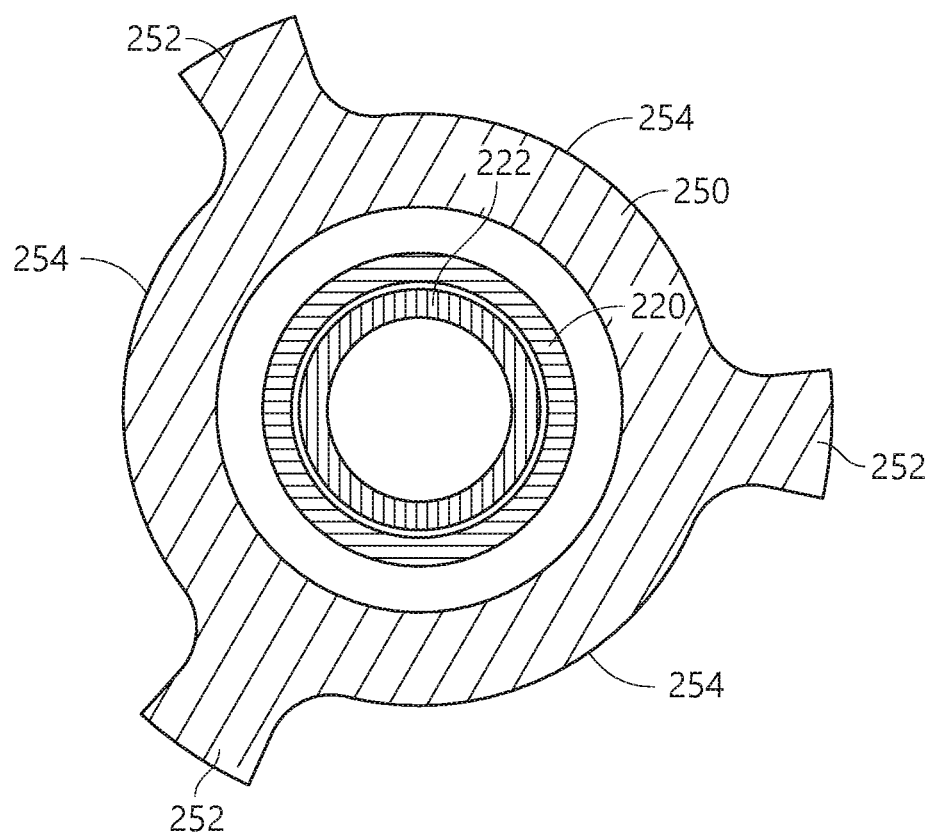
FIG. 7E is a cross-sectional view taken along section lines 7E-7E of FIG. 7D illustrating a structure of a proximal enclosure of the distal carrier assembly of the delivery device of FIG. 6, according to some embodiments.
Figure 10B:
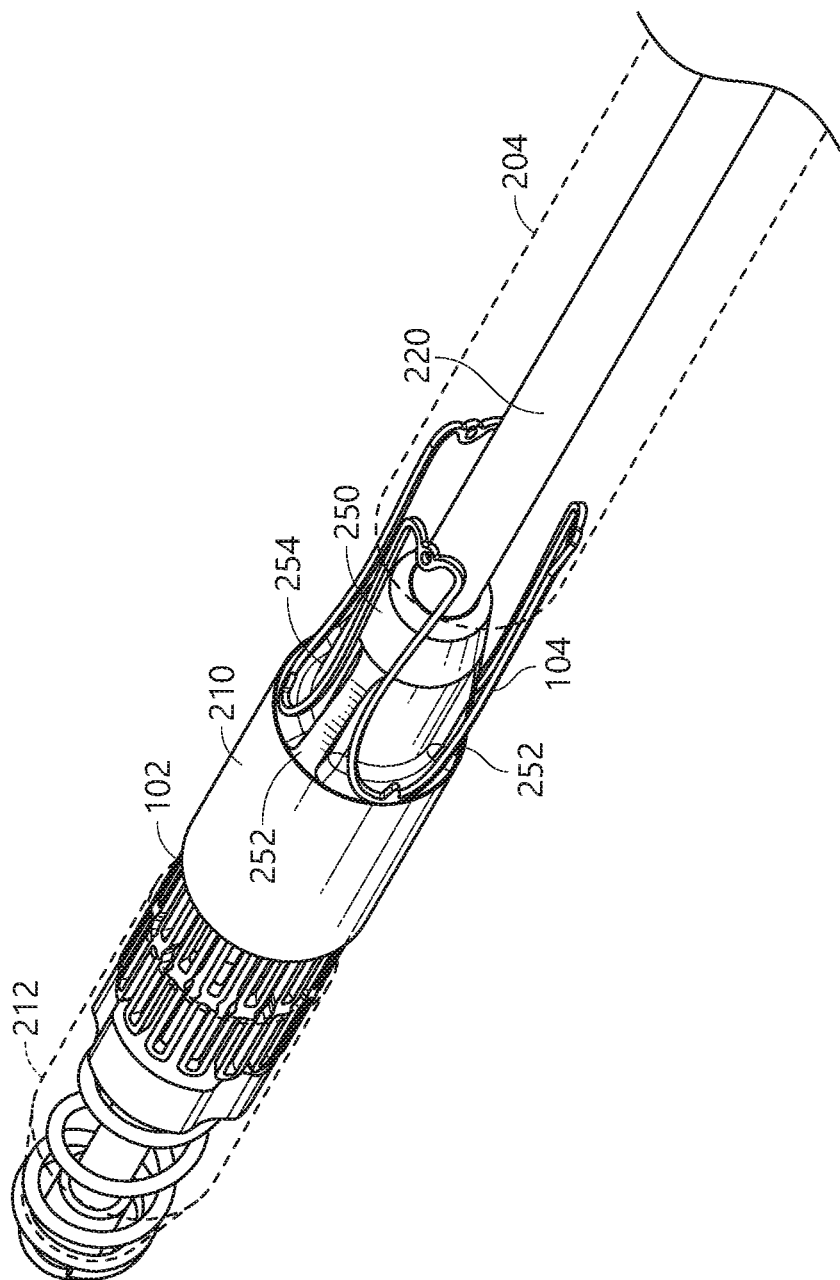

Referring to FIGS. 7E, 10A, and 10B, the proximal section 250 of the proximal enclosure 210 can include features that facilitate engagement and alignment of the proximal section 250 with the valve anchor. As illustrated in FIGS. 7E and 10A, the proximal section 250 of the proximal enclosure 210 has circumferential nodes 252 and circumferential cavities 254. Each of the circumferential cavities 254 may be defined by a space between two of the circumferential nodes 252. As illustrated in FIG. 10B, respective U-shaped members of the valve anchor 104 may be received in the circumferential cavities 254, between the circumferential nodes 252.

For example, when the valve anchor 104 is loaded and the proximal sheath component 204 covers the valve anchor 104, each U-shaped member of the valve anchor 104 may be positioned in a corresponding circumferential cavity 254, between the proximal section 250 and the proximal sheath component 204. The cross-sectional of the proximal section 250 of the proximal enclosure 210 illustrated in FIG. 7E (taken along lines 7E-7E of FIG. 7D) also shows that each of the circumferential cavities 254 may be defined by a space between two of the circumferential nodes 252, such that the valve anchor 104 may be received or positioned in the circumferential cavities 254.

The circumferential nodes 252 and the circumferential cavities 254 may facilitate realignment of the proximal sheath component 204 relative to the proximal enclosure 210 along a longitudinal axis of the delivery device 200. The proximal section 250 may be conical or tapered in a proximal direction, thereby facilitating alignment of the proximal sheath component 204 relative to the proximal enclosure 210 along a longitudinal axis of the delivery device 200. In the examples illustrated in FIGS. 7E, 10A, and 10B, the proximal section 250 has three circumferential nodes 252 and three circumferential cavities 254. However, in another example, a different number of the circumferential nodes 252 and/or a different number of the circumferential cavities 254 may be implemented.

As discussed above, the delivery device 200 provide several benefits, such as a compact passing profile that allows the delivery device 200 to move through the vasculature with facility, reliable control and positioning of the valve anchor while for within the native valve annulus and sinuses, predictable relative positioning of the support frame 102 and the valve anchor 104 via the link mechanism 160, and snag-free retrieval of the delivery device 200.

Illustration of Subject Technology as Clauses

Various examples of aspects of the disclosure are described as clause sets having numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause Set 1: Features of a Valve Prosthesis Delivery Device

Clause 1. A valve prosthesis delivery device for delivering a valve prosthesis, the valve prosthesis comprising a valve frame and a valve anchor, the delivery device comprising: an elongate core member extending along a longitudinal axis of the system; a proximal sheath component slidably coupled to the core member and comprising a proximal sheath lumen, the proximal sheath component being configured to receive at least a portion of the valve anchor within the proximal sheath lumen, the proximal sheath being proximally retractable relative to the core member for permitting expansion of the valve anchor; a distal carrier assembly comprising a distal enclosure and a proximal enclosure, the distal enclosure being coupled to the core member and comprising a distal lumen, the distal enclosure being configured to receive a distal portion of the valve frame within the distal lumen in a compressed configuration, the proximal enclosure being coupled to the core member proximal to the distal enclosure and comprising a proximal lumen, the proximal enclosure being configured to receive a proximal portion of the valve frame within the proximal lumen in a compressed configuration; and a plunger mechanism and a biasing means disposed within the distal lumen of the distal carrier assembly, the plunger mechanism being moveable between a distal position and a proximal position within the distal lumen, the plunger mechanism being biased toward the proximal position by the biasing means for urging the valve frame out of the distal lumen.

Clause 2. The delivery device of Clause 1, wherein the plunger mechanism comprises a plunger head that is moveable between the distal position and the proximal position within the distal lumen, the plunger head being biased toward the proximal position by the biasing means.

Clause 3. The delivery device of Clause 2, wherein in the proximal position, the plunger head extends at least partially proximally out of the distal lumen.

Clause 4. The delivery device of Clause 2, wherein in the proximal position, an outer surface of the plunger head is in contact with both the inner surface of the distal lumen and an inner surface of the proximal lumen when the proximal enclosure is distally advanced over the plunger head.

Clause 5. The delivery device of Clause 2, further comprising the valve prosthesis, wherein when the valve frame is positioned within the distal lumen, the plunger head is urged to the distal position.

Clause 6. The delivery device of Clause 2, wherein the biasing means comprises a spring.

Clause 7. The delivery device of Clause 6, wherein the biasing means comprises a spring, the spring being interposed between a proximal face of the distal enclosure and a distal face of the plunger head.

Clause 8. The delivery device of any preceding Clause wherein the plunger mechanism comprises a proximal portion that tapers in a proximal direction.

Clause 9. The delivery device of Clause 8, wherein the plunger mechanism comprises a plunger head with a plurality of petals extending from the plunger head, wherein the plurality of petals each form a ramped surface.

Clause 10. The delivery device of Clause 9, wherein the plurality of petals are configured to deflect radially inward within the distal lumen.

Clause 11. The delivery device of Clause 9, wherein the plurality of petals are configured to deflect radially outward when a portion of the plurality of petals exits the distal enclosure.

Clause 12. The delivery device of Clause 11, wherein in the proximal position, the plunger mechanism extends at least partially proximally out of the distal lumen, the proximal enclosure being distally advanceable over the ramped surfaces of the plurality of petals to align an outer surface of the distal enclosure with an outer surface of the proximal enclosure for facilitating removal of the delivery device from a patient.

Clause 13. A valve prosthesis delivery device for delivering a valve prosthesis, the valve prosthesis comprising a valve frame and a valve anchor, the delivery device comprising: an elongate core member extending along a longitudinal axis of the system; a sheath component slidably coupled to the core member and comprising a sheath lumen, the sheath component being configured to receive at least a portion of the valve anchor within the sheath lumen, the sheath being moveable relative to the core member for permitting expansion of the valve anchor; a plurality of grasper components disposed within the sheath component and extending along the elongate core member, wherein a distal end of the plurality of grasper components each engage with the valve anchor for permitting expansion of the valve anchor; and a distal hub disposed near a distal end of the elongate core member, wherein the distal hub is coupled to the plurality of grasper components to align each of the distal ends of the plurality of grasper components in a common plane as the sheath component is bent.

Clause 14. The valve prosthesis delivery device of Clause 13, wherein the distal hub is bonded to a tubular enclosure of each of the plurality of grasper components.

Clause 15. The valve prosthesis delivery device of Clause 13 or 14, wherein the distal hub comprises a plurality of passages to permit the plurality of grasper components to pass therethrough.

Clause 16. The valve prosthesis delivery device of Clause 13-15, wherein the distal hub comprises a core member passage to permit the elongate core member to pass therethrough.

Clause 17. The valve prosthesis delivery device of Clause 16, wherein the core member passage is offset from a central axis of the distal hub.

Clause 18. The valve prosthesis delivery device of Clause 13-17, wherein the distal hub is located approximately 1 to 4 inches from the distal end of at least one of the plurality of grasper components.

Clause 19. The valve prosthesis delivery device of Clause 13-18, wherein the distal hub is movable relative to the elongate core member.

Clause 20. The valve prosthesis delivery device of Clause 13-19, wherein the distal hub comprises a generally cylindrical shape.

Clause Set 2: Additional Features of a Valve Prosthesis Delivery Device

Clause 1. A valve prosthesis delivery device for delivering a valve prosthesis, the valve prosthesis comprising a valve frame and a valve anchor, the delivery device comprising: an elongate core member extending along a longitudinal axis of the system; a proximal sheath component slidably coupled to the core member and comprising a proximal sheath lumen, the proximal sheath component being configured to receive at least a portion of the valve anchor within the proximal sheath lumen, the proximal sheath being proximally retractable relative to the core member for permitting expansion of the valve anchor; and a distal carrier assembly comprising a distal enclosure and a proximal enclosure, the distal enclosure being coupled to the core member and comprising a distal lumen, the distal enclosure being configured to receive a distal portion of the valve frame within the distal lumen in a compressed configuration, the proximal enclosure being coupled to the core member proximal to the distal enclosure and comprising a proximal lumen, the proximal enclosure being configured to receive a proximal portion of the valve frame within the proximal lumen in a compressed configuration.

Clause 2. The delivery device of Clause 1, further comprising a plunger mechanism and a biasing means disposed within the distal lumen of the distal carrier assembly, the plunger mechanism being moveable between a distal position and a proximal position within the distal lumen, the plunger mechanism being biased toward the proximal position by the biasing means for urging the valve frame out of the distal lumen.

Clause 3. The delivery device of Clause 2, wherein the plunger mechanism comprises a plunger head that is moveable between the distal position and the proximal position within the distal lumen, the plunger head being biased toward the proximal position by the biasing means.

Clause 4. The delivery device of Clause 3, wherein in the proximal position, the plunger head extends at least partially proximally out of the distal lumen.

Clause 5. The delivery device of Clause 3, wherein in the proximal position, an outer surface of the plunger head is in contact with both the inner surface of the distal lumen and an inner surface of the proximal lumen when the proximal enclosure is distally advanced over the plunger head.

Clause 6. The delivery device of Clause 3, further comprising the valve prosthesis, wherein when the valve frame is positioned within the distal lumen, the plunger head is urged to the distal position.

Clause 7. The delivery device of Clause 3, wherein the biasing means comprises a spring.

Clause 8. The delivery device of Clause 7, wherein the biasing means comprises a spring, the spring being interposed between a proximal face of the distal enclosure and a distal face of the plunger head.

Clause 9. The delivery device of Clause 2, wherein the plunger mechanism comprises a proximal portion that tapers in a proximal direction.

Clause 10. The delivery device of Clause 9, wherein the proximal portion comprises a conical shape.

Clause 11. The delivery device of Clause 9, wherein in the proximal position, the plunger mechanism extends at least partially proximally out of the distal lumen, the proximal enclosure being distally advanceable over the tapered proximal portion of the plunger mechanism to align an outer surface of the distal enclosure with an outer surface of the proximal enclosure for facilitating removal of the delivery device from a patient.

Clause 12. The delivery device of any preceding Clause, wherein the distal enclosure comprises a distal nose cone that tapers in a distal direction.

Clause 13. The delivery device of any preceding Clause, further comprising the valve prosthesis, wherein in a loaded configuration, a proximal end of the distal enclosure is spaced longitudinally apart from a distal end of the proximal enclosure to permit a longitudinal section of the valve frame to remain exposed in the loaded configuration.

Clause 14. The delivery device of any preceding Clause, further comprising the valve prosthesis.

Clause 15. The delivery device of any preceding Clause, wherein the proximal enclosure comprises a proximal section having an outer diameter smaller than an inner diameter of the proximal lumen, and wherein when a valve anchor is loaded onto the delivery device, the valve anchor extends between the proximal section and the proximal sheath in a loaded configuration.

Clause 16. The delivery device of Clause 15, wherein the proximal section tapers in a proximal direction.

Clause 17. The delivery device of Clause 15, wherein the proximal section has a plurality of circumferential nodes, the plurality of circumferential nodes extending proximally from a proximal abutment surface of the proximal enclosure.

Clause 18. The delivery device of Clause 17, wherein the plurality of circumferential nodes comprises three circumferential nodes that are evenly circumferentially spaced apart from each other.

Clause 19. The delivery device of Clause 17, wherein the valve anchor comprises a plurality of U-shaped members, and wherein the proximal section has a plurality of circumferential cavities each configured to receive a respective U-shaped member of the valve anchor when the valve anchor is loaded onto the delivery device in a compressed configuration.

Clause 20. The delivery device of Clause 19, wherein, when the valve anchor is loaded onto the delivery device, each of the U-shaped members is positioned adjacent to a respective one of the plurality of circumferential cavities between the proximal section and the proximal sheath component.

Clause 21. The delivery device of Clause 20, wherein in a delivery configuration, the proximal enclosure is spaced apart from the distal enclosure by a gap to permit a portion of the valve frame to be exposed through the gap.

Clause 22. The delivery device of Clause 21, wherein the valve prosthesis includes a link mechanism interconnecting the valve anchor and the valve frame, and wherein the link mechanism extends through the gap, the link mechanism being moveable relative to the valve frame after releasing the valve anchor from the proximal sheath component.

Clause 23. A valve prosthesis delivery device for delivering a valve prosthesis, the valve prosthesis comprising a valve frame and a valve anchor, the delivery device comprising: an elongate core member extending along a longitudinal axis of the system; a sheath component slidably coupled to the core member and comprising a sheath lumen, the sheath component being configured to receive at least a portion of the valve anchor within the sheath lumen, the sheath being moveable relative to the core member for permitting expansion of the valve anchor; and a carrier assembly comprising a distal enclosure and a proximal enclosure, the enclosure being coupled to the core member and comprising a distal lumen, the enclosure being configured to receive a distal portion of the valve frame within the distal lumen in a compressed configuration, the proximal enclosure being coupled to the core member proximal to the enclosure and comprising a proximal lumen, the proximal enclosure being configured to receive a proximal portion of the valve frame within the proximal lumen in a compressed configuration.

Clause 24. The delivery device of Clause 23, wherein the sheath component is positioned proximally relative to the carrier assembly.

Clause 25. The delivery device of Clause 23, comprising any of the features recited in any of Clauses 1-21.

Clause 26. A method for delivering a prosthetic heart valve prosthesis to a native valve structure of a patient, the valve prosthesis comprising a valve frame and a valve anchor, the method comprising: introducing the valve prosthesis into the patient at an implantation site via a valve prosthesis delivery device, the system comprising a proximal sheath component and a distal carrier assembly, the proximal sheath component receiving at least a portion of the valve anchor in a proximal sheath lumen, and the distal carrier assembly comprising a distal enclosure and a proximal enclosure, the distal enclosure being configured to receive at least a distal portion of the valve frame; proximally retracting the proximal sheath in a proximal direction to permit expansion of the valve anchor; and expanding the distal carrier assembly to permit expansion of the valve frame.

Clause 27. The method of Clause 26, further comprising distally urging a base portion of the valve anchor into engagement with a native valve structure.

Clause 28. The method of Clause 26 or 27, further comprising proximally retracting the valve frame relative to the valve anchor to engage a link mechanism therebetween and restricting a range of movement of the valve frame relative to the valve anchor.

Clause 29. The method of Clause 28, further comprising distally advancing the valve frame.

Clause 30. The method of Clause 26, wherein the expanding longitudinally separating the distal enclosure from the proximal enclosure to permit expansion of the distal portion of the valve frame.

Clause 31. The method of Clause 26-30, wherein the expanding comprises distally advancing the distal enclosure relative to the proximal enclosure to permit expansion of the distal portion of the valve frame.

Clause 32. The method of Clause 26-31, wherein the expanding comprises proximally retracting the proximal enclosure relative to the distal enclosure to permit expansion of the proximal portion of the valve frame.

Clause 33. The method of Clause 26-32, wherein the expanding comprises proximally retracting the distal enclosure relative to the proximal enclosure and distally advancing the proximal enclosure relative to the distal enclosure to move the distal carrier assembly to a retrieval configuration for retracting the valve prosthesis delivery device from the patient.

Clause 34. The method of Clause 26-33, further comprising extending a plunger mechanism at least partially proximally out of the distal enclosure toward the proximal enclosure, aligning an outer surface of the distal enclosure with an outer surface of the proximal enclosure.

Clause 35. The method of Clause 26-34, wherein the proximal enclosure comprises a proximal section having an outer diameter smaller than the proximal enclosure, and wherein when a valve anchor is loaded onto the delivery device, the valve anchor extends between the proximal section and the proximal sheath in a loaded configuration.

Clause 36. The method of Clause 35, wherein the proximal section tapers in a proximal direction.

Clause 37. A method for delivering a prosthetic heart valve prosthesis to a native valve structure of a patient, the method comprising: introducing the valve prosthesis into the patient at an implantation site via a valve prosthesis delivery device, the valve prosthesis comprising a valve frame coupled to a valve anchor via a link mechanism, the valve prosthesis being carried by the delivery device; permitting expansion of the valve anchor; and with the valve anchor expanded, proximally retracting the valve frame within and relative to the valve anchor to proximally slide the link mechanism along the valve anchor toward an engagement region of the valve anchor for capturing the link mechanism in the engagement region for restricting a range of movement of the valve frame relative to the valve anchor.

Clause 38. The method of Clause 37, wherein the delivery device comprises a proximal sheath component and a distal carrier assembly, the proximal sheath component receiving at least a portion of the valve anchor in a proximal sheath lumen, and wherein the permitting expansion of the valve anchor comprises proximally retracting the proximal sheath in a proximal direction relative to the valve anchor to permit expansion of the valve anchor.

Clause 39. The method of Clause 38, the distal carrier assembly comprising a distal enclosure and a proximal enclosure.

Clause 40. The method of Clause 38, further comprising distally advancing the valve frame into the valve anchor.

Clause 41. The method of Clause 38, further comprising expanding the distal carrier assembly to permit expansion of the valve frame.

Clause 42. The method of Clause 38, wherein the distally advancing the valve frame into the valve anchor comprises distally advancing the valve frame until further distal movement of the valve frame relative to the valve anchor is restricted by the link mechanism.

Clause 43. The method of Clause 37-42, further comprising distally advancing the valve frame to pull the valve anchor distally relative to the native valve structure.

Clause 44. The method of Clause 37-43, further comprising rotating the valve frame, to rotationally adjust a position of the valve anchor relative to the native valve structure.

Clause 45. The method of Clause 37-44, wherein the permitting expansion of the valve frame comprises proximally retracting a proximal sheath of a delivery device to permit expansion of a base portion of the valve anchor.

Clause 46. The method of Clause 45, wherein a peak portion of the valve anchor is coupled to a grasper mechanism of a delivery device, and wherein distally urging the base portion of the valve anchor comprises distally advancing the grasper mechanism to convey a distal force to the valve anchor.

Clause 47. The method of Clause 45, wherein a base portion of the valve anchor is coupled to a grasper mechanism of a delivery device, and wherein distally urging the base portion of the valve anchor comprises distally advancing the grasper mechanism to convey a distal force to the valve anchor.

Clause 48. The method of Clause 38, wherein the permitting expansion of the valve frame comprises proximally retracting a proximal enclosure of the distal carrier assembly to expose a proximal portion of the valve frame.

Clause 49. The method of Clause 48, wherein the permitting expansion of the valve frame further comprises permitting a plunger mechanism to proximally urge a distal portion of the valve frame out of a distal enclosure of the distal carrier assembly to facilitate release of the valve frame from the distal carrier assembly.

Clause 50. The method of Clause 49, wherein the distal carrier assembly comprises a distal lumen and the plunger mechanism has a plunger head and biasing means disposed within the distal lumen, the plunger head being biased in a proximal direction by the biasing means, and wherein the permitting expansion of the valve frame comprises permitting the plunger head to move proximally within the distal lumen and to exert a proximally oriented force on the valve frame to release the valve frame from the distal lumen.

Clause 51. The method of Clause 49, wherein after the valve frame has been released, the method further comprises distally advancing the proximal enclosure over a proximal conical portion of the plunger mechanism to align an outer surface of the proximal enclosure with an outer surface of the distal enclosure of the distal carrier assembly.

Clause 52. The method of Clause 51, wherein the distally advancing the proximal enclosure over a proximal conical portion comprises abutting a distal end of the proximal enclosure against a proximal end of the distal enclosure.

FURTHER CONSIDERATIONS

In some embodiments, any of the clauses herein may depend from any one of the independent clauses or any one of the dependent clauses. In some embodiments, any of the clauses (e.g., dependent or independent clauses) may be combined with any other one or more clauses (e.g., dependent or independent clauses). In some embodiments, a claim may include some or all of the words (e.g., steps, operations, means or components) recited in a clause, a sentence, a phrase or a paragraph. In some embodiments, a claim may include some or all of the words recited in one or more clauses, sentences, phrases or paragraphs. In some embodiments, some of the words in each of the clauses, sentences, phrases or paragraphs may be removed. In some embodiments, additional words or elements may be added to a clause, a sentence, a phrase or a paragraph. In some embodiments, the subject technology may be implemented without utilizing some of the components, elements, functions or operations described herein. In some embodiments, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the term "distal" can denote a location or direction that is away from a point of interest, such as a control unit or region of the delivery system that will be used to deliver a valve prosthesis to a native valve annulus. Additionally, the term "proximal" can denote a location or direction that is closer to a point of interest, such as a control unit or region of the delivery system that will be used to deliver a valve prosthesis.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A valve prosthesis delivery device for delivering a valve prosthesis, the valve prosthesis comprising a valve frame and a valve anchor, the delivery device comprising:
   an elongate core member extending along a longitudinal axis of the device;
   a distal carrier assembly comprising a distal enclosure and a proximal enclosure, the distal enclosure being coupled to the core member and comprising a distal lumen, the distal enclosure being configured to receive a distal portion of the valve frame within the distal lumen in a compressed configuration, the proximal enclosure being coupled to the core member proximal to the distal enclosure and comprising a proximal lumen, the proximal enclosure being configured to receive a proximal portion of the valve frame within the proximal lumen in a compressed configuration;
   a sheath component having a sheath lumen configured to receive the valve anchor, wherein in a delivery configuration, the sheath component supports the valve anchor in a position longitudinally spaced apart from and proximal to the proximal lumen of the proximal enclosure, the sheath component being proximally retractable along the core member relative to the proximal enclosure for permitting expansion of the valve anchor; and
   a plunger mechanism and a biasing means disposed within the distal lumen of the distal carrier assembly, the plunger mechanism being moveable between a distal position and a proximal position within the distal lumen, the plunger mechanism being biased toward the proximal position by the biasing means for urging the valve frame out of the distal lumen.

2. The delivery device of claim 1, wherein the plunger mechanism comprises a plunger head that is moveable between the distal position and the proximal position within the distal lumen, the plunger head being biased toward the proximal position by the biasing means.

3. The delivery device of claim 2, wherein in the proximal position, the plunger head extends at least partially proximally out of the distal lumen.

4. The delivery device of claim 2, wherein in the proximal position, an outer surface of the plunger head is in contact with both an inner surface of the distal lumen and an inner surface of the proximal lumen when the proximal enclosure is distally advanced over the plunger head.

5. The delivery device of claim 2, further comprising the valve prosthesis, wherein when the valve frame is positioned within the distal lumen, the plunger head is urged to the distal position.

6. The delivery device of claim 2, wherein the biasing means comprises a spring.

7. The delivery device of claim 6, wherein the biasing means comprises a spring, the spring being interposed between a proximal face of the distal enclosure and a distal face of the plunger head.

8. The delivery device of claim 1, wherein the plunger mechanism comprises a proximal portion that tapers in a proximal direction.

9. The delivery device of claim 8, wherein the plunger mechanism comprises a plunger head with a plurality of petals extending from the plunger head, wherein the plurality of petals each form a ramped surface.

10. The delivery device of claim 9, wherein the plurality of petals are configured to deflect radially inward within the distal lumen.

11. The delivery device of claim 9, wherein the plurality of petals are configured to deflect radially outward when a portion of the plurality of petals exits the distal enclosure.

12. The delivery device of claim 11, wherein in the proximal position, the plunger mechanism extends at least partially proximally out of the distal lumen, the proximal enclosure being distally advanceable over the ramped surfaces of the plurality of petals to align an outer surface of the distal enclosure with an outer surface of the proximal enclosure for facilitating removal of the delivery device from a patient.

13. The delivery device of claim 1, wherein the sheath lumen and the proximal lumen of the proximal enclosure have about the same diameter.

14. A valve prosthesis delivery device for delivering a valve prosthesis, the valve prosthesis comprising a valve frame and a valve anchor, the delivery device comprising:
an elongate core member;
a distal carrier assembly being coupled to the core member and comprising a distal enclosure and a proximal enclosure, the distal enclosure having a distal lumen configured to receive a distal portion of the valve frame therein, the proximal enclosure having a proximal lumen configured to receive a proximal portion of the valve frame therein;
a sheath component comprising a sheath lumen configured to receive at least a portion of the valve anchor and a distal end portion that is configured to proximally abut the proximal enclosure, the sheath component being proximally retractable relative to the proximal enclosure for permitting expansion of the valve anchor;
a plunger mechanism; and
a biasing means disposed within the distal lumen of the distal carrier assembly, the plunger mechanism being moveable between a distal position and a proximal position within the distal lumen, the plunger mechanism being biased toward the proximal position by the biasing means for urging the valve frame out of the distal lumen.

15. The delivery device of claim 14, wherein the proximal enclosure comprises a proximal section that extends within the sheath lumen when the sheath component distal end portion abuts the proximal enclosure.

16. The delivery device of claim 14, wherein the sheath component encloses the valve anchor therein when the sheath component abuts the proximal enclosure.

17. A valve prosthesis delivery device for delivering a valve prosthesis, the valve prosthesis comprising a valve frame and a valve anchor, the delivery device comprising:
an elongate core member extending along a longitudinal axis of the device;
a distal carrier assembly being coupled to the core member and comprising a distal enclosure and a proximal enclosure, proximal to the distal enclosure, the distal enclosure comprising a distal lumen configured to receive a distal portion of the valve frame, the proximal enclosure comprising a proximal lumen configured to receive a proximal portion of the valve frame; and
a plunger mechanism and a biasing means disposed within the distal lumen of the distal carrier assembly, the plunger mechanism being moveable between a distal position and a proximal position within the distal lumen, the plunger mechanism being biased toward the proximal position by the biasing means for urging the valve frame out of the distal lumen, wherein the plunger mechanism comprises a plunger head with a plurality of petals extending from the plunger head.

18. The delivery device of claim 17, wherein each of the plurality of petals comprises a ramped surface.

19. The delivery device of claim 18, wherein each of the plurality of petals is configured to deflect radially inward within the distal lumen.

20. The delivery device of claim 18, wherein each of the plurality of petals is configured to deflect radially outward when a portion of the plurality of petals exits the distal enclosure.

21. The delivery device of claim 20, wherein each of the plurality of petals comprises an engagement tooth configured to engage with the distal enclosure in the proximal position such that the plunger mechanism extends proximally out of the distal lumen and the proximal enclosure is distally advanceable over the ramped surfaces of the plurality of petals to align an outer surface of the distal enclosure with an outer surface of the proximal enclosure for facilitating removal of the delivery device from a patient.

* * * * *